US008273356B2

(12) United States Patent
Morsey et al.

(10) Patent No.: US 8,273,356 B2
(45) Date of Patent: Sep. 25, 2012

(54) ANTI-IGE VACCINES

(75) Inventors: Mohamad A. Morsey, Niantic, CT (US); Michael G. Sheppard, Victoria (AU); David W. Wheeler, Richland, MI (US)

(73) Assignee: Pfizer Inc., Madison, NJ (US)

( * ) Notice: Subject to any disclaimer, the term of this patent is extended or adjusted under 35 U.S.C. 154(b) by 0 days.

(21) Appl. No.: 12/624,566

(22) Filed: Nov. 24, 2009

(65) Prior Publication Data

US 2010/0113361 A1 May 6, 2010

Related U.S. Application Data

(63) Continuation of application No. 11/196,897, filed on Aug. 4, 2005, which is a continuation of application No. 10/751,743, filed on Jan. 5, 2004, now abandoned, which is a continuation of application No. 09/938,700, filed on Aug. 24, 2001, now Pat. No. 6,887,472.

(60) Provisional application No. 60/228,989, filed on Aug. 30, 2000.

(51) Int. Cl.
  *A61K 39/00* (2006.01)
(52) U.S. Cl. .................. 424/192.1; 424/134.1; 424/805; 424/810; 530/387.3; 530/862; 435/328; 536/23.1
(58) Field of Classification Search .................. None
  See application file for complete search history.

(56) References Cited

U.S. PATENT DOCUMENTS

| 4,208,479 | A | 6/1980 | Zuk et al. |
|---|---|---|---|
| 4,980,286 | A | 12/1990 | Morgan et al. |
| 5,436,146 | A | 7/1995 | Shenk et al. |
| 5,601,821 | A | 2/1997 | Stanworth et al. |
| 5,629,415 | A | 5/1997 | Hollis et al. |
| 5,653,980 | A | 8/1997 | Hellman |
| 5,965,709 | A | 10/1999 | Presta et al. |
| 6,734,287 | B1 | 5/2004 | Lawton et al. |
| 6,887,472 | B2 | 5/2005 | Morsey et al. |
| 6,913,749 | B2 | 7/2005 | Hellman |
| 6,974,572 | B2 | 12/2005 | Morsey et al. |
| 2004/0146504 | A1 | 7/2004 | Morsey et al. |

FOREIGN PATENT DOCUMENTS

| EP | 0028815 | | 5/1981 |
|---|---|---|---|
| EP | 0 263 655 | | 4/1988 |
| EP | 0263655 | A2 * | 4/1988 |
| EP | 0 957 111 | | 11/1999 |
| JP | 09169795 | | 6/1997 |
| WO | 88/00204 | | 1/1988 |
| WO | 92/06180 | | 4/1992 |
| WO | 92/20316 | | 11/1992 |
| WO | 92/20360 | | 11/1992 |
| WO | 92/22635 | | 12/1992 |
| WO | 93/05810 | | 4/1993 |
| WO | 93/14188 | | 7/1993 |
| WO | 93/20221 | | 10/1993 |
| WO | 98/08598 | | 4/1994 |
| WO | 94/12649 | | 6/1994 |
| WO | 97/30156 | | 8/1997 |
| WO | 97/31948 | | 9/1997 |
| WO | 98/24808 | | 6/1998 |
| WO | 99/67293 | | 12/1999 |
| WO | 99/67642 | | 12/1999 |
| WO | 00/23477 | | 4/2000 |
| WO | 00/25722 | | 5/2000 |

OTHER PUBLICATIONS

Chang, TW Nat Biotechnol. Feb. 2000;18(2):157-62.*
Harlow et al., "Antibodies, A Laboratory Manual", 1998, Cold Spring Harbor Laboratory Publication, Cold Spring Harbor, NY, p. 129.
Partial European Search Report, EP 09154655.6 dated Apr. 24, 2009 (9 pages).
Extended European Search Report, EP 08156885.9 dated Dec. 10, 2008 (9 pages).
Kozarsky and Wilson, "Gene therapy: adenovirus vectors", Current Opinion in Genetics and Development, 3:499-503, 1993.
Shakib et al., "Identification of Peptide Motifs Recognized by a Human IgG Autoanti-IgE Antibody Using a Phase Display Library", Clinical and Experimental Allergy, 30(7):1041-1046, 2000.
Burt and Stanworth, "Inhibition of binding of rat IgE to rat mast cells by synthetic IgE peptides", Eur. J. Immunol., 17:437-440, 1987.
Helm et al., "The mast cell binding site on human immunoglobulin E", Nature, 331:180-183, 1988.
Helm et al., "Blocking of passive sensitization of human mast cells and basophil granulocytes with IgE antibodies by a recombinant human {epsilon}-chain fragment of 76 amino acids", Proc. Natl. Acad. Sci. USA, 86:9465-9469, 1989.
Vercelli et al., "The B-cell binding site on human immunoglobulin E", Nature, 338:649-651, 1989.
Nio et al., "Inhibition of passive sensitization of human peripheral basophils by synthetic human immunoglobulin E peptide fragments", FEBS 319(3):225-228, 1993. Nio et al., "Inhibition of passive cutaneous anaphylaxis by synthetic human immunoglobulin E peptide fragments", FEBS 314(3):229-231, 1992.
Basu et al., "Purification and Characterization of Human Recombinant IgE-Fc Fragments That Bind to the Human High Affinity IgE Receptor",J. Biol. Chem., 268(18):13118-13127, 1993.
Vangelista et al., "The immunoglobulin-like modules C{epsilon}3 and {alpha}2 are the minimal units necessary for human IgE-Fc{epsilon}RI interaction", J. Clin. Invest., 103(11):1571-1578, 1999.
Robertson and Liu, "IgE Structure-Function Relationships Defined by Sequence Directed Antibodies Induced by Synthetic Peptides", Molecular Immunology, 25(2):103-113, 1988.
Schwarzbaum et al., "Mapping of murine IgE epitopes involved in IgE-Fc{epsilon} receptor interactions", Eur. J. Immunol., 19:1015-1023, 1989.

(Continued)

*Primary Examiner* — Michael Szperka
(74) *Attorney, Agent, or Firm* — Gloria K. Szakiel; Barbara L. Renda

(57) ABSTRACT

The present invention provides compositions and methods for the use of antigenic peptides derived from the Fc portion of the epsilon heavy chain of an IgE molecule as vaccines for the treatment and prevention of IgE-mediated allergic disorders. In particular, the invention provides compositions, methods for the treatment and prevention of IgE-mediated allergic disorders comprising an immunogenic amount of one or more antigenic peptides derived from the CH3 domain or junction of Ch-3/CH4 domain of an IgE molecule and methods for the evaluation of IgE mediated allergies in dogs.

10 Claims, 5 Drawing Sheets

OTHER PUBLICATIONS

Weetall et al., "Mapping the Site of Interaction Between Murine IgE and Its High Affinity Receptor with Chimeric Ig", The Journal of Immunology, 145(11):3849-3854, 1990.
Presta et al., "The Binding Site on Human Immunoglobulin E for Its High Affinity Receptor", J. Biol. Chem., 269 (42):26368-26373, 1994.
Nissim et al., "Fine Specificity of the IgE Interaction with the Low and High Affinity Fc Receptor", The Journal of Immunology, 150(4):1365-1374, 1993.
Moscoso Del Prado et al., "Monoclonal Antibodies Against Human IgE. Identification of an Epitope Sharing Properties with the High-Affinity Receptor Binding Site", Molecular Immunology, 28(8):839-844, 1991.
Keegan et al., "Characterization of New Rat Anti-Mouse IgE Monoclonals and Their Use Along With Chimeric IgE to Further Define the Site That Interacts With Fc{epsilon}RII and Fc{epsilon}RI", Molecular Immunology, 28 (10):1149-1154, 1991.
Hook et al., "Monoclonal Antibodies Defining Epitopes on Human IgE", Molecular Immunology, 28(6):631-639, 1991.
Takemoto et al., "Anti-Human IgE Monoclonal Antibodies Recognizing Epitopes Related to the Binding Sites of High and Low Affinity IgE Receptors", Microbiol. Immunol., 38(1):63-71, 1994.
Baniyash et al., "Anti-IgE Monoclonal Antibodies Directed at the Fc{epsilon} Receptor Binding Site", Molecular Immunology, 25(8):705-711, 1988.
Chang, "The pharmacological basis of anti-IgE therapy", Nature Biotechnology, 18:157-162, 2000.
Presta et al., "Humanization of an Antibody Directed Against IgE", The Journal of Immunology, 151(5):2623-2632, 1993.
Stadler et al., "Biological Activities of Anti-IgE Antibodies", Int. Arch. Allergy Immunol., 102:121-126, 1993.
Rudolf et al., "Epitope-Specific Antibody Response to IgE by Mimotope Immunization", The Journal of Immunology, 160:3315-3321, 1998.
Li et al., "A murine model of IgE-mediated cow's mulk hypersensitivity", J. Allergy Clin. Immunol., 103:206-214, 1999.
Li et al., "Murine model of atopic dermatitis associated with food hypersensitivity", J. Allergy Clin. Immunol., 107:693-702, 2001.
Ermel et al., "The Atopic Dog: A Model for Food Allergy", Laboratory Animal Science, 47(1):40-49, 1997.
McDermott et al., "Identification, cloning, and characterization of a major cat flea salivary allergen (Cte f 1)", Molecular Immunology, 37:361-375, 2000.
Underwood et al., "IgE production, antigen-induced airway inflammation and airway hyperreactivity in the Brown Norway rat: the effects of ricin", Immunology, 85:256-261, 1995.
Underwood et al., "Ricin Increases IgE Levels and Airway Inflammation but Not Hyperresponsiveness in the Rat", Int. Arch. Allergy Immunol., 107:119-121, 1995.
Diaz-Sanchez et al., "Generation of a long-lived IgE response in high and low responder strains of rat by co-administration of ricin and antigen", Immunology, 72:297-303, 1991.
Noble et al., "Elimination of IgE regulatory rat CD8+ T cells in vivo increases the co-ordinate expression of Th2 cytokines IL-4, IL-5 and IL-10", Immunology, 80:326-329, 1993.
Diaz-Sanchez et al., "Ricin enhances IgE responses by inhibiting a subpopulation of early-activated IgE regulatory CD8+ T cells", Immunology, 78:226-236, 1993.
Karlin and Altschul, "Methods for assessing the statistical significance of molecular sequence features by using general scoring schemes", Proc. Natl. Acad. Sci. USA, 87:2264-2268, 1990.
Karlin and Altschul, "Applications and statistics for multiple high-scoring segments in molecular sequences", Proc. Natl. Acad. Sci. USA, 90:5873-5877, 1993.
Pearson and Lipman, "Improved tools for biological sequence comparison", Proc. Natl. Acad. Sci. USA, 85:2444-2448, 1988.
Benoist and Chambon, "In vivo sequence requirements of the SV40 early promoter region", Nature, 290:304-310, 1981.
Yamamoto et al., "Identification of a Functional Promoter in the Long Terminal Repeat of Rous Sarcoma Virus", Cell, 22:787-797, 1980.
Wagner et al., "Nucleotide sequence of the thymidine kinase gene of herpes simplex virus type 1", Proc. Natl. Acad. Sci. USA, 78(3):1441-1445, 1981.
Brinster et al., "Regulation of metallothionein-thymidine kinase fusion plasmids injected into mouse eggs", Nature, 296(5852):39-42, 1982.
Villa-Komaroff et al., "A bacterial clone synthesizing proinsulin", Proc. Natl. Acad. Sci. USA, 75(8):3727-3731, 1978.
De Boer et al., "The tac promoter: A functional hybrid derived from the trp and lac promoters", Proc. Natl. Acad. Sci. USA, 80:21-25, 1983.
Gilbert and Villa-Komaroff, "Useful Proteins from Recombinant Bacteria", Sci. Am., 242(4):74-94, 1980.
Torelli and Robotti, "Advance and Adam: two algorithms for the analysis of global similarity between homologous informational sequences", Comput. Appl. Biosci., 10(1):3-6, 1994.
Herrera-Estrella et al., "Expression of chimaeric genes transferred into plant cells using a Ti-plasmid-derived vector", Nature, 303:209-213, 1983.
Gardner et al., "The complete nucleotide sequence of an infectious clone of cauliflower mosaic virus by M13mp7 shotgun sequencing", Nucleic Acids Research, 9(12):2871-2888, 1981.
Herrera-Estrella et al., "Light-inducible and chloroplast-associated expression of a chimaeric gene introduced into *Nicotiana tabacum* using a Ti plasmid vector", Nature, 310:115-120, 1984.
Rheinwald, "Serial Cultivation of Normal Human Epidermal Keratinocytes", Methods in Cell Biology, 21A:229-255, 1980.
Pittelkow and Scott, "New Techniques for the In Vitro Culture of Human Skin Keratinocytes and Perspectives on Their Use for Grafting of Patients With Extensive Burns", Mayo Clin. Proc., 61:771-777, 1986.
Langer, "New Methods of Drug Delivery", Science, 249:1527-1533, 1990.
Treat et al., "Liposome Encapsulated Doxorubicin Preliminary Results of Phase I and Phase II Trials", Liposomes in the Therapy of Infectious Diseases and Cancer, 353-365, 1989.
Sefton, "Implantable Pumps", Critical Reviews in Biomedical Engineering, 14(3):201-240, 1987.
Buchwald et al., "Long-term, continuous intravenous heparin administration by an implantable infusion pump in ambulatory patients with recurrent venous thrombosis", Surgery, 88(4):507-516, 1980.
Saudek et al., "A Preliminary Trial of the Programmable Implantable", The New England Journal of Medicine, 321:574-579, 1989.
Levy et al., "Inhibition of Calcification of Bioprosthetic Heart Valves by Local Controlled-Release Diphosphonate", Science, 228:190-192, 1985.
During et al., "Controlled Release of Dopamine from a Polymeric Brain Implant: In Vivo Characterization", Ann. Neurol., 25:351-356, 1989.
Howard III et al., "Intracerebral drug delivery in rats with lesion-induced memory deficits", J. Neurosurg., 71:105-112, 1989.
Goodson, Chapter 6: Dental Applications, pp. 115-138 from Medical Applications of Controlled Release, vol. II: Applications and Evaluation, Langer and Wise (eds.), CRC Press, Inc., Boca Raton, FL, 1984.
Joliot et al., "Antennapedia homeobox peptide regulates neural morphogenesis", Proc. Natl. Acad. Sci. USA, 88:1864-1868, 1991.
Langer and Peppas, "Chemical and Physical Structure of Polymers as Carriers for Controlled Release of Bioactive Agents: A Review", JMS-Rev. Macromol. Chem. Phys., C23(1):61-126, 1983.
Swift et al., "Tissue-Specific Expression of the Rat Pancreatic Elastase I Gene in Transgenic Mice", Cell, 38:639-646, 1984.
Ornitz et al., "Elastase I Promoter Directs Expression of Human Growth Hormone and SV40 T Antigen Genes to Pancreatic Acinar Cells in Transgenic Mice", Cold Spring Harb. Symp. Quant. Biol., 50:399-409, 1985.
MacDonald, "Expression of the Pancreatic Elastase I Gene in Transgenic Mice", Hepatology, 7(1):42S-51S, 1987.
Hanahan, "Heritable formation of pancreatic {beta}-cell tumours in transgenic mice expressing recombinant insulin/simian virus 40 oncogenes", Nature, 315:115-122, 1985.

Grosschedl et al., "Introduction of a {mu} Immunoglobulin Gene into the Mouse Germ Line: Specific Expression in Lymphoid Cells and Synthesis of Functional Antibody", Cell, 38:647-658, 1984.

Adams et al., "The c-myc oncogene driven by immunoglobulin enhancers induces lymphoid malignancy in transgenic mice", Nature, 318:533-538, 1985.

Alexander et al., "Expression of the c-myc Oncogene under Control of an Immunoglobulin Enhancer in E{mu}-myc Transgenic Mice", Molecular and Cellular Biology, 7(4):1436-1444, 1987.

Leder et al., "Consequences of Widespread Deregulation of the c-myc Gene in Transgenic Mice: Multiple Neoplasms and Normal Development", Cell, 45:485-495, 1986.

Pinkert et al., "An albumin enhancer located 10 kb upstream functions along with its promoter to direct efficient, liver-specific expression in transgenic mice", Genes & Development, 1:268-276, 1987.

Krumlauf et al., "Developmental Regulation of {alpha}-Fetoprotein Genes in Transgenic Mice", Molecular and Cellular Biology, 5(7):1639-1648, 1985.

Hammer et al., "Diversity of Alpha-Fetoprotein Gene Expression in Mice Is Generated by a Combination of Separate Enhancer Elements", Science, 235:53-58, 1987.

Kelsey et al., "Species- and tissue-specific expression of human {alpha}1-antitrypsin in transgenic mice", Genes & Development, 1:161-171, 1987.

Magram et al., "Developmental regulation of a cloned adult {beta}-globin gene in transgenic mice", Nature, 315:338-340, 1985.

Kollias et al., "Regulated Expression of Human A{gamma}-, {beta}-, and Hybrid {gammabeta}-Globin Genes in Transgenic Mice: Manipulation of the Developmental Expression Patterns", Cell, 46:89-94, 1986.

Readhead et al., "Expression of a Myelin Basic Protein Gene in Transgenic Shiverer Mice: Correction of the Dysmyelinating Phenotype", Cell, 48:703-712, 1987.

Shani, "Tissue-specific expression of rat myosin light-chain 2 gene in transgenic mice", Nature, 314:283-286, 1985.

Reecy et al., "Multiple Regions of the Porcine {alpha}-Skeletal Actin Gene Modulate Muscle-Specific Expression in Cell Culture and Directly Injected Skeletal Muscle", Animal Biotechnology, 9(2):101-120, 1998.

Mason et al., "The Hypogonadal Mouse: Reproductive Functions Restored by Gene Therapy", Science, 234:1372-1378, 1986.

Wigler et al., "Transfer of Purified Herpes Virus Thymidine Kinase Gene to Cultured Mouse Cells", Cell, 11:223-232, 1977.

Szybalska and Szybalski, "Genetics of Human Cell Lines, IV. DNA-Mediated Heritable Transformation of a Biochemical Trait", Proc. Natl. Acad. Sci. USA, 48:2026-2034, 1962.

Lowy et al., "Isolation of Transforming DNA: Cloning the Hamster aprt Gene", Cell, 22:817-823, 1980.

Wigler et al., "Transformation of mammalian cells with an amplifiable dominant-acting gene", Proc. Natl. Acad. Sci. USA, 77(5):3567-3570, 1980.

O'Hare et al., "Transformation of mouse fibroblasts to methotrexate resistance by a recombinant plasmid expressing a prokaryotic dihydrofolate reductase", Proc. Natl. Acad. Sci. USA, 78(3):1527-1531, 1981.

Mulligan and Berg, "Selection for animal cells that express the *Escherichia coli* gene coding for xanthine-guanine phosphoribosyltransferase", Proc. Natl. Acad. Sci. USA, 78(4):2072-2076, 1981.

Colbere-Garapin et al., "A New Dominant Hybrid Selective Marker for Higher Eukaryotic Cells", J. Mol. Biol., 150:1-14, 1981.

Santerre et al., "Expression of prokaryotic genes for hygromycin B and G418 resistance as dominant-selection markers in mouse L cells", Gene, 30:147-156, 1984.

Goldspiel et al., "Human gene therapy", Clin. Pharm., 12:488-505, 1993.

Wu and Wu, "Delivery systems for gene therapy", Biotherapy, 3:87-95, 1991.

Tolstoshev, "Gene Therapy, Concepts, Current Trials and Future Directions", Annu. Rev. Pharmacol. Toxicol., 32:573-596, 1993.

Mulligan, "The Basic Science of Gene Therapy", Science, 260:926-932, 1993.

Morgan and Anderson, "Human Gene Therapy", Annu. Rev. Biochem., 62:191-217, 1993.

Robinson, "Gene therapy—proceeding from laboratory to clinic", Trends in Biotechnology, 11(5):155-215, 1993.

Koller and Smithies, "Inactivating the {beta}2-microglobulin locus in mouse embryonic stem cells by homologous recombination", Proc. Natl. Acad. Sci. USA, 86:8932-8935, 1989.

Zijlstra et al., "Germ-line transmission of a disrupted {beta}2-microglobulin gene produced by homologous recombination in embryonic stem cells", Nature, 342:435-438, 1989.

Wu and Wu, "Receptor-mediated in Vitro Gene Transformation by a Soluble DNA Carrier System", The Journal of Biological Chemistry, 262(10):4429-4432, 1987.

Miller et al., "Use of Retroviral Vectors for Gene Transfer and Expression", Methods in Enzymology, 217:581-599, 1993.

Clowes et al., "Long-Term Biological Response of Injured Rat Carotid Artery Seeded with Smooth Muscle Cells Expressing Retrovirally Introduced Human Genes", J. Clin. Invest., 93:644-651, 1994.

Kiem et al., "Retrovirus-Mediated Gene Transduction Into Canine Peripheral Blook Repopulating Cells", Blood, 83 (6):1467-1473, 1994.

Salmons and Gunzburg, "Targeting of Retroviral Vectors for Gene Therapy", Human Gene Therapy, 4:129-141, 1993.

Grossman and Wilson, "Retroviruses: delivery vehicle to the liver", Current Opinion in Genetics and Development, 3:110-114, 1993.

Bout et al., "Lung Gene Therapy: In Vivo Adenovirus-Mediated Gene Transfer to Rhesus Monkey Airway Epithelium", Human Gene Therapy, 5:3-10, 1994.

Rosenfeld et al., "Adenovirus-Mediated Transfer of a Recombinant {alpha}1-Antitrypsin Gene to the Lung Epithelium in Vivo", Science, 252:431-434, 1991.

Rosenfeld et al., "In Vivo Transfer of the Human Cystic Fibrosis Transmembrane Conductance Regulator Gene to the Airway Epithelium", Cell, 68:143-155, 1992.

Mastrangeli et al., "Diversity of Airway Epithelial Cell Targets for In Vivo Recombinant Adenovirus-mediated Gene Transfer", The Journal of Clinical Investigation, 91:225-234, 1993.

Wang et al., "A packaging cell line for propagation of recombinant adenovirus vectors containing two lethal gene-region deletions", Gene Therapy, 2:775-783, 1995.

Walsh et al., "Gene Therapy for Human Hemoglobinopathies", P.S. E.B.M., 204:289-300, 1993.

Loeffler and Behr, "Gene Transfer into Primary and Established Mammalian Cell Lines with Lipopolyamine-Coated DNA", Methods in Enzymology, 217:599-618, 1993.

Cotten et al., "Receptor-Mediated Transport of DNA into Eukaryotic Cells", Methods in Enzymology, 217:618-644, 1993.

Cline, "Perspectives for Gene Therapy: Inserting New Genetic Information into Mammalian Cells by Physical Techniques and Viral Vectors", Pharmac. Ther., 29:69-92, 1985.

Stemple et al., "Isolation of a Stem Cell for Neurons and Glia from the Mammalian Neural Crest", Cell, 71:973-985, 1992.

* cited by examiner

Figure 1. ELISA reactivity of sera from rabbits immunized with IgE peptides
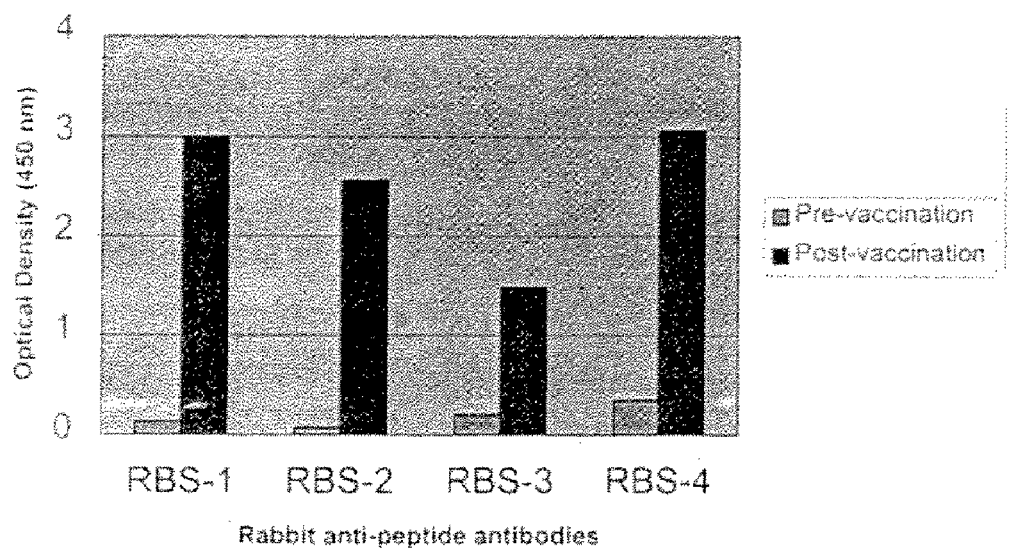
Figure 2. ELISA reactivity of rabbit anti-peptide antibodies against canine IgE
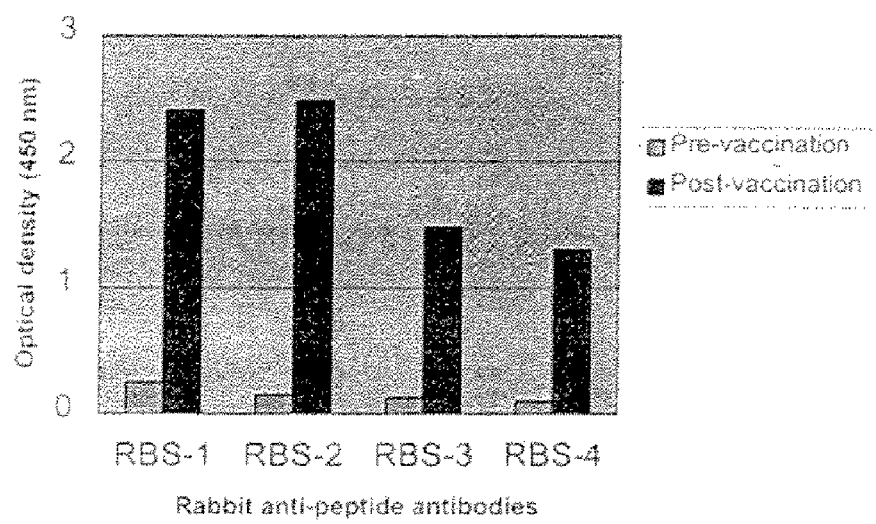

FIGURE 3

SEQ ID NO 1: NH$_2$-CSESDPRGVTSYLSPPSPLDLYVHKAPKIT-COOH

FIGURE 4

SEQ ID NO 2 : NH$_2$-CLVVDLATMEGMNLTWYRESKEPVNPGPLNK-COOH

FIGURE 5

SEQ ID NO 3: NH$_2$-KDHFNGTITVTSTLPVNTNDWIEGETYY-COOH

FIGURE 6

SEQ ID NO 4: NH$_2$-CRVTHPHLPKDIVRSIAKAPGKRAP-COOH

FIGURE 7

SEQ ID NO 5: NH$_2$-LSPPSPLDLYVHKAPKITCLVVDLATME-COOH

FIGURE 8

SEQ ID NO 6:
NH$_2$-CGMNLTWYRESKEPVNPGPLNKKDHFNGTITVTS-COOH

FIGURE 9

SEQ ID NO 7: NH$_2$-TLPVNTNDWIEGETYYCRVTHPHLPK-COOH

FIGURE 10
SEQ ID NO 8: NH$_2$-CADSNPRGVSAYLSRPSPFDLFIRKSPTIT-COOH

FIGURE 11
SEQ ID NO 9:
NH$_2$-CLVVDLAPSKGTVNLTWSRASGKPVNHSTRKEE-COOH

FIGURE 12
SEQ ID NO: 10: NH$_2$-KQRNGTLTVTSTLPVGTRDWIEGETYQ-COOH

FIGURE 13
SEQ ID NO: 11: NH$_2$-CRVTHPHLPRALMRSTTKTSGPRAAP-COOH

FIGURE 14
SEQ ID 12: NH$_2$-SRPSPFDLFIRKSPTITCLVVDLAPSK-COOH

FIGURE 15
SEQ ID NO: 13:
NH$_2$-GTVNLTWSRASGKPVNHSTRKEEKQRNGTLTVTS-COOH

FIGURE 16
SEQ ID NO: 14: NH$_2$-TLPVGTRDWIEGETYQCRVTHPHLPR-COOH

FIGURE 17

SEQ ID NO 15:

TGCTCTGACCCGCGTGGTGTTACCTCTTACCTGTCTCCGCCGTCTCCGCTGGAC
CTGTACGTTCACAAAGCTCCGAAAATCACC

FIGURE 18

SEQ ID NO 16:

TGCCTGGTAGTGGACCTGGCCACCATGGAAGGCATGAACCTGACCTGGTACCG
GGAGAGCAAAGAACCCGTGAACCCGGGCCCTTTGAACAAG

FIGURE 19

SEQ ID NO 17:

TGCAAGGATCACTTCAATGGGACGATCACAGTCACGTCTACCCTGCCAGTGAAC
ACCAATGACTGGATCGAGGGCGAGACCTACTAT

FIGURE 20

SEQ ID NO 18:

TGCAGGGTGACCCACCCGCACCTGCCCAAGGACATCGTGCGCTCCATTGCCAA
GGCCCCTGGTAAGCGTGCCCCC

FIGURE 21

SEQ ID NO 19:

CTGTCTCCGCCGTCTCCGCTGGACCTGTACGTTCACAAAGCTCCGAAAATCACC
TGCCTGGTAGTGGACCTGGCCACCATGGAA

FIGURE 22

SEQ ID NO 20:

TGCGGCATGAACCTGACCTGGTACCGGGAGAGCAAAGAACCCGTGAACCCGG
GCCCTTTGAACAAGAAGGATCACTTCAATGGGACGATCACAGTCACGTCT

FIGURE 23

SEQ ID NO 21:

ACCCTGCCAGTGAACACCAATGACTGGATCGAGGGCGAGACCTACTATTGCAG
GGTGACCCACCCGCACCTGCCCAAG

FIGURE 24

SEQ ID NO 22:

TGCGCGGACAGCAACCCGAGAGGGGTGAGCGCCTACCTAAGCCGGCCCAGCC
CGTTCGACCTGTTCATCCGCAAGTCGCCCACGATCACC

FIGURE 25

SEQ ID NO 23:

TGTCTGGTGGTGGACCTGGCACCCAGCAAGGGGACCGTGAACCTGACCTGGTC
CCGGGCCAGTGGGAAGCCTGTGAACCACTCCACCAGAAAGGAGGAG

FIGURE 26

SEQ ID NO 24:

AAGCAGCGCAATGGCACGTTAACCGTCACGTCCACCCTGCCGGTGGGCACCCG
AGACTGGATCGAGGGGGAGACCTACCAG

FIGURE 27

SEQ ID NO 25:

TGCAGGGTGACCCACCCCACCTGCCCAGGGCCCTCATGCGGTCCACGACCA
AGACCAGCGGCCCGCGTGCTGCCCCG

FIGURE 28

SEQ ID NO 26:

AGCCGGCCCAGCCCGTTCGACCTGTTCATCCGCAAGTCGCCCACGATCACCTG
TCTGGTGGTGGACCTGGCACCCAGCAAG

FIGURE 29

SEQ ID NO 27:

GGGACCGTGAACCTGACCTGGTCCCGGGCCAGTGGGAAGCCTGTGAACCACT
CCACCAGAAAGGAGGAGAAGCAGCGCAATGGCACGTTAACCGTCACGTCC

FIGURE 30

SEQ ID NO 28:

ACCCTGCCGGTGGGCACCCGAGACTGGATCGAGGGGGAGACCTACCAGTGCA
GGGTGACCCACCCCACCTGCCCAGG

SEQUENCE LISTING

```
<160> NUMBER OF SEQ ID NOS: 28

<210> SEQ ID NO 1
<211> LENGTH: 30
<212> TYPE: PRT
<213> ORGANISM: Artificial Sequence
<220> FEATURE:
<223> OTHER INFORMATION: DOG CH3/CH4 PEPTIDE SEQUENCE

<400> SEQUENCE: 1

Cys Ser Glu Ser Asp Pro Arg Gly Val Thr Ser Tyr Leu Ser Pro Pro
1               5                   10                  15

Ser Pro Leu Asp Leu Tyr Val His Lys Ala Pro Lys Ile Thr
            20                  25                  30

<210> SEQ ID NO 2
<211> LENGTH: 31
```

```
<212> TYPE: PRT
<213> ORGANISM: Artificial Sequence
<220> FEATURE:
<223> OTHER INFORMATION: DOG CH3/CH4 PEPTIDE SEQUENCE

<400> SEQUENCE: 2

Cys Leu Val Val Asp Leu Ala Thr Met Glu Gly Met Asn Leu Thr Trp
1               5                   10                  15

Tyr Arg Glu Ser Lys Glu Pro Val Asn Pro Gly Pro Leu Asn Lys
            20                  25                  30

<210> SEQ ID NO 3
<211> LENGTH: 28
<212> TYPE: PRT
<213> ORGANISM: Artificial Sequence
<220> FEATURE:
<223> OTHER INFORMATION: DOG CH3/CH4 PEPTIDE SEQUENCE

<400> SEQUENCE: 3

Lys Asp His Phe Asn Gly Thr Ile Thr Val Thr Ser Thr Leu Pro Val
1               5                   10                  15

Asn Thr Asn Asp Trp Ile Glu Gly Glu Thr Tyr Tyr
            20                  25

<210> SEQ ID NO 4
<211> LENGTH: 25
<212> TYPE: PRT
<213> ORGANISM: Artificial Sequence
<220> FEATURE:
<223> OTHER INFORMATION: DOG CH3/CH4 PEPTIDE SEQUENCE

<400> SEQUENCE: 4

Cys Arg Val Thr His Pro His Leu Pro Lys Asp Ile Val Arg Ser Ile
1               5                   10                  15

Ala Lys Ala Pro Gly Lys Arg Ala Pro
            20                  25

<210> SEQ ID NO 5
<211> LENGTH: 28
<212> TYPE: PRT
<213> ORGANISM: Artificial Sequence
<220> FEATURE:
<223> OTHER INFORMATION: DOG CH3/CH4 PEPTIDE SEQUENCE

<400> SEQUENCE: 5

Leu Ser Pro Pro Ser Pro Leu Asp Leu Tyr Val His Lys Ala Pro Lys
1               5                   10                  15

Ile Thr Cys Leu Val Val Asp Leu Ala Thr Met Glu
            20                  25

<210> SEQ ID NO 6
<211> LENGTH: 34
<212> TYPE: PRT
<213> ORGANISM: Artificial Sequence
<220> FEATURE:
<223> OTHER INFORMATION: DOG CH3/CH4 PEPTIDE SEQUENCE

<400> SEQUENCE: 6

Cys Gly Met Asn Leu Thr Trp Tyr Arg Glu Ser Lys Glu Pro Val Asn
1               5                   10                  15

Pro Gly Pro Leu Asn Lys Lys Asp His Phe Asn Gly Thr Ile Thr Val
            20                  25                  30

Thr Ser
```

```
<210> SEQ ID NO 7
<211> LENGTH: 26
<212> TYPE: PRT
<213> ORGANISM: Artificial Sequence
<220> FEATURE:
<223> OTHER INFORMATION: DOG CH3/CH4 PEPTIDE SEQUENCE

<400> SEQUENCE: 7

Thr Leu Pro Val Asn Thr Asn Asp Trp Ile Glu Gly Glu Thr Tyr Tyr
1               5                   10                  15

Cys Arg Val Thr His Pro His Leu Pro Lys
            20                  25

<210> SEQ ID NO 8
<211> LENGTH: 30
<212> TYPE: PRT
<213> ORGANISM: Artificial Sequence
<220> FEATURE:
<223> OTHER INFORMATION: HUMAN CH3/CH4 PEPTIDE SEQUENCE

<400> SEQUENCE: 8

Cys Ala Asp Ser Asn Pro Arg Gly Val Ser Ala Tyr Leu Ser Arg Pro
1               5                   10                  15

Ser Pro Phe Asp Leu Phe Ile Arg Lys Ser Pro Thr Ile Thr
            20                  25                  30

<210> SEQ ID NO 9
<211> LENGTH: 33
<212> TYPE: PRT
<213> ORGANISM: Artificial Sequence
<220> FEATURE:
<223> OTHER INFORMATION: HUMAN CH3/CH4 PEPTIDE SEQUENCE

<400> SEQUENCE: 9

Cys Leu Val Val Asp Leu Ala Pro Ser Lys Gly Thr Val Asn Leu Thr
1               5                   10                  15

Trp Ser Arg Ala Ser Gly Lys Pro Val Asn His Ser Thr Arg Lys Glu
            20                  25                  30

Glu

<210> SEQ ID NO 10
<211> LENGTH: 27
<212> TYPE: PRT
<213> ORGANISM: Artificial Sequence
<220> FEATURE:
<223> OTHER INFORMATION: HUMAN CH3/CH4 PEPTIDE SEQUENCE

<400> SEQUENCE: 10

Lys Gln Arg Asn Gly Thr Leu Thr Val Thr Ser Thr Leu Pro Val Gly
1               5                   10                  15

Thr Arg Asp Trp Ile Glu Gly Glu Thr Tyr Gln
            20                  25

<210> SEQ ID NO 11
<211> LENGTH: 26
<212> TYPE: PRT
<213> ORGANISM: Artificial Sequence
<220> FEATURE:
<223> OTHER INFORMATION: HUMAN CH3/CH4 PEPTIDE SEQUENCE

<400> SEQUENCE: 11

Cys Arg Val Thr His Pro His Leu Pro Arg Ala Leu Met Arg Ser Thr
1               5                   10                  15

Thr Lys Thr Ser Gly Pro Arg Ala Ala Pro
            20                  25
```

<210> SEQ ID NO 12
<211> LENGTH: 27
<212> TYPE: PRT
<213> ORGANISM: Artificial Sequence
<220> FEATURE:
<223> OTHER INFORMATION: HUMAN CH3/CH4 PEPTIDE SEQUENCE

<400> SEQUENCE: 12

Ser Arg Pro Ser Pro Phe Asp Leu Phe Ile Arg Lys Ser Pro Thr Ile
1               5                   10                  15

Thr Cys Leu Val Val Asp Leu Ala Pro Ser Lys
            20                  25

<210> SEQ ID NO 13
<211> LENGTH: 34
<212> TYPE: PRT
<213> ORGANISM: Artificial Sequence
<220> FEATURE:
<223> OTHER INFORMATION: HUMAN CH3/CH4 PEPTIDE SEQUENCE

<400> SEQUENCE: 13

Gly Thr Val Asn Leu Thr Trp Ser Arg Ala Ser Gly Lys Pro Val Asn
1               5                   10                  15

His Ser Thr Arg Lys Glu Glu Lys Gln Arg Asn Gly Thr Leu Thr Val
            20                  25                  30

Thr Ser

<210> SEQ ID NO 14
<211> LENGTH: 28
<212> TYPE: PRT
<213> ORGANISM: Artificial Sequence
<220> FEATURE:
<223> OTHER INFORMATION: HUMAN CH3/CH4 PEPTIDE SEQUENCE

<400> SEQUENCE: 14

Thr Leu Pro Val Gly Thr Arg Asp Trp Ile Glu Gly Glu Thr Tyr Gln
1               5                   10                  15

Cys Arg Val Thr His Pro His Leu Pro Arg Cys His
            20                  25

<210> SEQ ID NO 15
<211> LENGTH: 84
<212> TYPE: DNA
<213> ORGANISM: Artificial Sequence
<220> FEATURE:
<223> OTHER INFORMATION: DOG CH3/CH4 NUCLEOTIDE SEQUENCE

<400> SEQUENCE: 15
tgctctgacc cgcgtggtgt tacctcttac ctgtctccgc cgtctccgct ggacctgtac      60
gttcacaaag ctccgaaaat cacc                                            84

<210> SEQ ID NO 16
<211> LENGTH: 93
<212> TYPE: DNA
<213> ORGANISM: Artificial Sequence
<220> FEATURE:
<223> OTHER INFORMATION: DOG CH3/CH4 NUCLEOTIDE SEQUENCE

<400> SEQUENCE: 16
tgcctggtag tggacctggc caccatggaa ggcatgaacc tgacctggta ccgggagagc      60
aaagaacccg tgaacccggg ccctttgaac aag                                  93

```
<210> SEQ ID NO 17
<211> LENGTH: 87
<212> TYPE: DNA
<213> ORGANISM: Artificial Sequence
<220> FEATURE:
<223> OTHER INFORMATION: DOG CH3/CH4 NUCLEOTIDE SEQUENCE

<400> SEQUENCE: 17
tgcaaggatc acttcaatgg gacgatcaca gtcacgtcta ccctgccagt gaacaccaat     60
gactggatcg agggcgagac ctactat                                        87

<210> SEQ ID NO 18
<211> LENGTH: 75
<212> TYPE: DNA
<213> ORGANISM: Artificial Sequence
<220> FEATURE:
<223> OTHER INFORMATION: DOG CH3/CH4 NUCLEOTIDE SEQUENCE

<400> SEQUENCE: 18
tgcagggtga cccacccgca cctgcccaag gacatcgtgc gctccattgc caaggcccct     60
ggtaagcgtg ccccc                                                     75

<210> SEQ ID NO 19
<211> LENGTH: 84
<212> TYPE: DNA
<213> ORGANISM: Artificial Sequence
<220> FEATURE:
<223> OTHER INFORMATION: DOG CH3/CH4 NUCLEOTIDE SEQUENCE

<400> SEQUENCE: 19
ctgtctccgc cgtctccgct ggacctgtac gttcacaaag ctccgaaaat cacctgcctg     60
gtagtggacc tggccaccat ggaa                                           84

<210> SEQ ID NO 20
<211> LENGTH: 102
<212> TYPE: DNA
<213> ORGANISM: Artificial Sequence
<220> FEATURE:
<223> OTHER INFORMATION: DOG CH3/CH4 NUCLEOTIDE SEQUENCE

<400> SEQUENCE: 20
tgcggcatga acctgacctg gtaccgggag agcaaagaac ccgtgaaccc gggcccttg      60 aacaagaagg atcacttcaa tgggacgatc acagtcacgt ct                       102

<210> SEQ ID NO 21
<211> LENGTH: 78
<212> TYPE: DNA
<213> ORGANISM: Artificial Sequence
<220> FEATURE:
<223> OTHER INFORMATION: DOG CH3/CH4 NUCLEOTIDE SEQUENCE

<400> SEQUENCE: 21
accctgccag tgaacaccaa tgactggatc gagggcgaga cctactattg cagggtgacc     60
cacccgcacc tgcccaag                                                  78

<210> SEQ ID NO 22
<211> LENGTH: 90
<212> TYPE: DNA
<213> ORGANISM: Artificial Sequence
<220> FEATURE:
<223> OTHER INFORMATION: DOG CH3/CH4 NUCLEOTIDE SEQUENCE

<400> SEQUENCE: 22
tgcgcggaca gcaacccgag aggggtgagc gcctacctaa gccggcccag cccgttcgac     60
```
ctgttcatcc gcaagtcgcc cacgatcacc                                             90

<210> SEQ ID NO 23
<211> LENGTH: 99
<212> TYPE: DNA
<213> ORGANISM: Artificial Sequence
<220> FEATURE:
<223> OTHER INFORMATION: DOG CH3/CH4 NUCLEOTIDE SEQUENCE

<400> SEQUENCE: 23
tgtctggtgg tggacctggc acccagcaag gggaccgtga acctgacctg gtcccgggcc           60
agtgggaagc ctgtgaacca ctccaccaga aaggaggag                                  99

<210> SEQ ID NO 24
<211> LENGTH: 81
<212> TYPE: DNA
<213> ORGANISM: Artificial Sequence
<220> FEATURE:
<223> OTHER INFORMATION: DOG CH3/CH4 NUCLEOTIDE SEQUENCE

<400> SEQUENCE: 24
aagcagcgca atggcacgtt aaccgtcacg tccaccctgc cggtgggcac ccgagactgg           60
atcgaggggg agacctacca g                                                    81

<210> SEQ ID NO 25
<211> LENGTH: 78
<212> TYPE: DNA
<213> ORGANISM: Artificial Sequence
<220> FEATURE:
<223> OTHER INFORMATION: DOG CH3/CH4 NUCLEOTIDE SEQUENCE

<400> SEQUENCE: 25
tgcagggtga cccacccca cctgcccagg gccctcatgc ggtccacgac caagaccagc            60
ggcccgcgtg ctgccccg                                                        78

<210> SEQ ID NO 26
<211> LENGTH: 81
<212> TYPE: DNA
<213> ORGANISM: Artificial Sequence
<220> FEATURE:
<223> OTHER INFORMATION: DOG CH3/CH4 NUCLEOTIDE SEQUENCE

<400> SEQUENCE: 26
agccggccca gcccgttcga cctgttcatc cgcaagtcgc ccacgatcac ctgtctggtg          60
gtggacctgg cacccagcaa g                                                    81

<210> SEQ ID NO 27
<211> LENGTH: 102
<212> TYPE: DNA
<213> ORGANISM: Artificial Sequence
<220> FEATURE:
<223> OTHER INFORMATION: DOG CH3/CH4 NUCLEOTIDE SEQUENCE

<400> SEQUENCE: 27
gggaccgtga acctgacctg gtcccgggcc agtgggaagc ctgtgaacca ctccaccaga          60
aaggaggaga agcagcgcaa tggcacgtta accgtcacgt cc                             102

<210> SEQ ID NO 28
<211> LENGTH: 78
<212> TYPE: DNA
<213> ORGANISM: Artificial Sequence
<220> FEATURE:
<223> OTHER INFORMATION: DOG CH3/CH4 NUCLEOTIDE SEQUENCE

```
<400> SEQUENCE: 28
accctgccgg tgggcacccg agactggatc gaggggggaga cctaccagtg cagggtgacc    60
cacccccacc tgcccagg                                                   78
```

US 8,273,356 B2

ANTI-IGE VACCINES

CROSS-REFERENCE TO RELATED APPLICATIONS

This application is a continuation of application Ser. No. 11/196,897, filed on Aug. 4, 2005, now pending; which is a continuation of application Ser. No. 10/751,743, filed on Jan. 5, 2004, now abandoned; which is a continuation of application Ser. No. 09/938,700, filed on Aug. 24, 2001, now U.S. Pat. No. 6,887,472; which claims the benefit of priority under 35 U.S.C. 119(e) to U.S. Provisional Application No. 60/228,989, filed on Aug. 30, 2000; the entire disclosures of which are incorporated herein by reference.

FIELD OF THE INVENTION

The present invention relates to compositions and methods for the use of antigenic peptides derived from the Fc portion of the epsilon heavy chain of an IgE molecule as vaccines for the treatment and prevention of IgE-mediated allergic disorders. In particular, the present invention relates to compositions comprising at least one antigenic peptide derived from the CH3 domain or CH3-CH4 domain junction of an IgE molecule optionally coupled to a heterologous carrier protein. The compositions of the present invention may also comprise an adjuvant. The compositions of the present invention induce anti-IgE antibodies, which bind to soluble (free) IgE in serum and other bodily fluids, but do not cross-link receptor-bound IgE. The present invention further relates to methods of administering compositions of the invention to animals, preferably mammals and most preferably humans, for the treatment or prevention of IgE-mediated allergic disorders and methods for evaluating vaccines and other therapies for the treating IgE-mediated allergic disorders.

BACKGROUND OF THE INVENTION

Immune-mediated allergic (hypersensitivity) reactions are classified into four types (I-IV) according to the underlying mechanisms leading to the expression of the allergic symptoms. Type I allergic reactions are characterized by IgE-mediated release of vasoactive substances such as histamine from mast cells and basophils. The release of these substances and the subsequent manifestation of allergic symptoms are initiated by the cross-linking of allergen-bound IgE to its receptor on the surface of mast cells and basophils.

An IgE antibody is a complex molecule consisting of two identical heavy chains and two identical light chains held together by disulfide bonds in a "Y" shape-configuration. Each light chain consists of a variable ($V_L$) domain linked to a constant domain ($C_L$), and each heavy chain consists of a variable domain (Vh) and four constant domains (CH1, CH2, CH3, and CH4, also known as C$\epsilon$1, C$\epsilon$2, C$\epsilon$3, and C$\epsilon$4; respectively). The two arms of an IgE antibody contain the site at which an IgE antibody binds to its specific antigen (allergen) and each arm is referred to as a Fab (fragment-antigen-binding) fragment. The tail of an IgE antibody is termed Fc (fragment-crystalline) as it can form crystals when separated from the Fab fragments of the antibody under appropriate experimental conditions. The Fc fragment of an IgE antibody consists of the C$\epsilon$2, C$\epsilon$3, and C$\epsilon$4 domains and contains the biologically active structures of the IgE antibody (e.g., receptor binding sites).

The production of IgE antibodies requires interactions and collaborations among three cells; antigen presenting cells (APC), T lymphocytes (T helper cells; Th) and antibody producing cells (B lymphocytes; B cells). When a foreign substance, an allergen, is introduced for the first time into the body of subjects (e.g., by inhalation of environmental allergen, ingestion of certain foods, or via the skin), the allergen is taken up by APCs (e.g., macrophages) which then digest or process the allergen into smaller fragments (epitopes). These fragments are displayed on the surface of APCs in association with specific molecules known as major histocompatibility complex proteins (MhC). The allergen fragment/MhC complex displayed on the surface of APCs is recognized and bound by receptors on the surface of specific T lymphocytes. This recognition and binding event leads to the activation of T lymphocytes and the subsequent expression and secretion of cytokines such as interleukin-4 (IL-4). These cytokines induce the multiplication, clonal expansion and differentiation of B cells specific for the allergen in question (i.e., B cell which express on their surface immunoglobulin receptors capable of binding to the allergen) and ultimately lead to the production of IgE antibodies from these B cells. A portion of the activated T lymphocytes and IgE producing B cells eventually become committed to a pool of cells called T and B memory cells, which are capable of faster recognition of allergen upon subsequent exposure to the allergen.

In individuals suffering from type I allergic reactions, exposure to an allergen for a second time leads to the production of high levels of IgE antibodies specific for the allergen as a result of the involvement of memory B and T cells in the 3-cell interaction required for IgE production. The high levels of IgE antibodies produced during the second exposure lead to cross-linking of IgE receptors on mast cells and basophils by allergen-bound IgE, which in turn leads to the activation of these cells and the release of the pharmacological mediators that are responsible for the clinical manifestations of type I allergic diseases.

Two receptors with differing affinities for IgE have been identified and characterized. The high affinity receptor (Fc$\epsilon$RI) is expressed on the surface of mast cells and basophils. The low affinity receptor (Fc$\epsilon$RII/CD23) is expressed on many cell types including B cells, T cells, macrophages, eosinophils and Langerhan cells. The high affinity IgE receptor consists of three subunits (alpha, beta and gamma chains). Several studies demonstrate that only the alpha chain is involved in the binding of IgE, whereas the beta and gamma chains (which are either transmembrane or cytoplasmic proteins) are required for signal transduction events. The identification of IgE structures required for IgE to bind to the Fc$\epsilon$RI on mast cells and basophils is of utmost importance in devising strategies for treatment or prevention of IgE-mediated allergies. For example, the elucidation of the IgE receptor-binding site could lead to the identification of peptides or small molecules that block the binding of IgE to receptor-bearing cells in vivo.

Over the last 15 years, a variety of approaches have been utilized to determine the Fc$\epsilon$RI binding site on IgE. These approaches can be classified into five different categories. In one approach, small peptides corresponding to portions of the Fc part of an IgE molecule were produced and analyzed for their ability to inhibit IgE from its receptors. See, for example, Nakamura et al., EP0263655 published Apr. 13, 1988, Burt et al., 1987, European Journal of Immunology, 17:437-440; helm et al., 1988, Nature 331:180-183; helm et al., 1989, PNAS 86:9465-9469; Vercelli et al., 1989, Nature 338:649-651; Nio et al., 1990, Peptide Chemistry, 2: 203-208; Nio et al., 1993, FEBS Lett. 319:225-228; and Nio et al., 1992, FEBS Lett. 314:229-231. Although many of the peptides described in these studies were shown to inhibit the binding of IgE to its receptors, different studies reported different sequences as being responsible for IgE binding.

helm et al. (1988, Nature 331:180-183) identified a 75 amino acid peptide that spans the junction between Cεh2 and Cεh3 domains of IgE and showed that this peptide binds to the IgE receptor with an affinity close to that of the native IgE molecule. On the other hand, Basu et al. (1993, Journal of Biological Chemistry 268: 13118-13127) expressed various fragments from IgE molecules and found that only those fragments containing both the CH3 and CH4 domains were able to bind IgE and that CH2 domain is not necessary for binding. Vangelista et al. (1999, Journal of Clinical Investigation 103:1571-1578) expressed only the CH3 domain of IgE and showed that this domain alone could bind to IgE receptor and prevent binding of IgE to its receptor. The results of Basu et al. and Vangelista et al. are inconsistent and conflict with those of helm et al. cited above.

In a second approach to identify the FcRI binding site on IgE, polyclonal antibodies against peptides corresponding to parts of the CH2 domain, CH3 domain or CH4 domain were produced and used to probe for receptor binding site on IgE (Robertson et al., 1988, Molecular Immunol. 25:103-118). Robertson et al. concluded that the amino acid residues defined by a peptide derived from the CH4 domain were not likely to be involved in receptor binding, whereas amino acid residues defined by a peptide derived from the CH3 domain of IgE were most likely proximal to the IgE receptor-binding site (amino acids 387-401). however, the anti-CH3 peptide antibodies released histamine from IgE-loaded mast cells indicating that the amino acids defined by the CH3 peptide did not define the bona fide IgE receptor-binding site and that anti-CH3 peptide antibodies could cause anaphylaxis.

In a third approach to identify the FcεRI binding site on IgE, several investigators produced IgE mutants in an attempt to identify the amino acid residues involved in receptor binding (see, e.g., Schwarzbaum et al., 1989, European Journal of immunology 19:1015-1023; Weetall et al., 1990, Journal of Immunology 145:3849-3854; and Presta et al., 1994, Journal of Biological Chemistry 269:26368-26373). Schwartzbaum et al. demonstrated that a mouse IgE antibody with the point mutation proline to histidine at amino acid residue 442 in the CH4 domain has a two fold reduced affinity for the IgE receptor. Schwartzbaum et al. concluded that the CH4 domain of an IgE antibody is involved in IgE binding to its receptor. however, Schwartzbaum's conclusion contradict Weetall et al.'s conclusion that the binding of mouse IgE to its high affinity receptor involves portions of the CH2 and CH3 domains of the IgE antibody, but not the CH4 domain. Further, Schwartzbaum et al.'s conclusions contradict Presta et al.'s conclusion that the amino acid residues of the IgE antibody important for binding to the FcεRI are located in the CH3 domain.

In a fourth approach to identify the FcεRI binding site on IgE, chimeric IgE molecules were constructed and analyzed for their ability to bind to the FcεRI. Weetall et al., supra constructed a series of chimeric murine IgE-human IgG molecules and tested their binding to the IgE receptor. Weetall et al., supra concluded that the CH4 domain does not participate in receptor binding and that the CH2 and CH3 domains are both required for binding to the high affinity receptor on mast cells. In another study, Nissim at al. (1993, Journal of Immunol 150:1365-1374) tested the ability of a series of human IgE-murine IgE chimera to bind to the FcεRI and concluded that only the CH3 domain is needed for binding to the FcεRI. The conclusion by Nissim at al. corroborates the conclusion by Vangelista et al. that the CH3 domain of IgE alone binds to the FcεRI. however, the conclusions by Nissim et al, and Vangelista et al. contradict the conclusions of Weetall at al. and Robertson at al.

Presta et al., supra produced chimeric human IgG in which the CH2 was replaced with CH3 from human IgE. When tested for receptor binding, this chimera bound to the FcεRI albeit with a four-fold reduced affinity compared with native IgE. The results of Presta at al. appear to corroborate with the results of Nissim et al., but conflict with those of Weetall et al., helm at al., and Basu et. al., cited above. In a further attempt to define the exact amino acid residues responsible for the binding of IgE to its receptor, Presta at al. inserted specific amino acid residues corresponding to CH2-CH3 hinge region and three loops from the CH3 domain of human IgE into their analogous locations within human IgG and called these mutants IgGEL. Unfortunately, when these IgGEL variants were tested for receptor binding, they exhibited minimal binding compared to the native IgE or the IgG in which the full length CH3 domain replaced the full length CH2 domain.

In a fifth approach to identify the FcεRI binding site on IgE, monoclonal antibodies have been developed and analyzed for their ability to block IgE binding to the FcεRI. See, for example, Del Prado at al., 1991, Molecular immunology 28:839-844; Keegan at al., 1991, Molecular Immunology 28:1149-1154; hook et al., 1991, Molecular Immunology 28:631-639; Takemoto et al., 1994, Microbiology and Immunology 38:63-71; and Baniyash et al., 1988, Molecular Immunology 25:705-711. Although many monoclonal antibodies have been developed, they have provided little information on the bona fide IgE receptor-binding site because in many cases the amino acid sequence recognized by these monoclonal antibodies have not or could not be identified. Further, the monoclonal antibodies developed may block IgE from binding to its receptor by steric hindrance or induction of severe conformational changes in the IgE molecule, rather than by the binding and masking of IgE residues directly involved in receptor binding.

It is apparent from the above discussion that approaches that have been devised to identify the receptor binding site on IgE have produced conflicting results. The difficulty in the identification of the amino acid residues of IgE responsible for receptor binding could be further complicated by the possibility that the site on IgE used for binding to the receptor may not be a linear sequence of amino acids, which could be mimicked by a synthetic peptide. Rather, the binding site may be a conformational determinant formed by multiple amino acids that are far apart in the IgE protein sequence which are brought into close proximity only in the native three-dimensional structure of IgE. Studies with IgE variants, IgE chimera, and monoclonal anti-IgE antibodies strongly suggest that the binding site is a conformational determinant.

Currently, IgE-mediated allergic reactions are treated with drugs such as antihistamines and corticosteroids which attempt to alleviate the symptoms associated with allergic reactions by counteracting the effects of the vasoactive substances released from mast cells and basophils. high doses of antihistamines and corticosteroids have serious side effects such as renal and gastrointestinal toxicities. Thus, other methods for treating type I allergic reactions are needed.

One approach to the treatment of type I allergic disorders has been the production of monoclonal antibodies which react with soluble (free) IgE in serum, block IgE from binding to its receptor on mast cells and basophils, and do not bind to receptor-bound IgE (i.e., they are non-anaphylactogenic). Two such monoclonal antibodies (rhuMab E25 and CGP56901) are in advanced stages of clinical development for treatment of IgE-mediated allergic reactions (see, e.g., Chang, T. W., 2000, Nature Biotechnology 18:157-62). The identity of the amino acid residues of the IgE molecule recognized by these monoclonal antibodies are not known and it is presumed that these monoclonal antibodies recognize conformational determinants on IgE.

Although early results from clinical trials with therapeutic anti-IgE monoclonal antibodies suggest that these therapies are effective in the treatment of atopic allergies, the use of monoclonal antibodies for long-term treatment of allergies has some significant shortcomings. First, since these monoclonal antibodies were originally produced in mice, they had to be reengineered so as to replace mouse sequences with consensus human IgG sequences (Presta et al., 1993, The Journal of Immunology 151:2623-2632). Although this "humanization" process has led to production of monoclonal antibodies that contain 95% human sequences, there remain some sequences of mouse origin. Since therapy with these anti-IgE antibodies requires frequent administration of the antibodies over a long period of time, some treated allergic patients could produce an antibody response against the mouse sequences that still remain within these therapeutic antibodies. The induction of antibodies against the therapeutic anti-IgE would negate the therapeutic impact of these anti-IgE antibodies at least in same patients. Second, the cost of treatment with these antibodies will be very high since high doses of these monoclonal antibodies are required to induce a therapeutic effect. Moreover, the frequency and administration routes with which these antibodies have to be administered is inconvenient. A more attractive strategy for the treatment of IgE-mediated disorders is the administration of peptides which induce the production of anti-IgE antibodies.

One of the most promising treatments for IgE-mediated allergic reactions is the active immunization against appropriate non-anaphylactogenic epitopes on endogenous IgE. Stanworth et al. (U.S. Pat. No. 5,601,821) described a strategy involving the use of a peptide derived from the CH4 domain of the human IgE coupled to a heterologous carrier protein as an allergy vaccine, however, this peptide has been shown not to induce the production of antibodies that react with native soluble IgE. Further, hellman (U.S. Pat. No. 5,653,980) proposed anti-IgE vaccine compositions based on fusion of full length CH2-CH3 domains (approximately 220 amino acid long) to a foreign carrier protein. however, the antibodies induced by the anti-IgE vaccine compositions proposed by hellman will most likely result in anaphylaxis since antibodies against some portions of the CH2 and CH3 domains of the IgE molecule have been shown to cross-link the IgE receptor on the surface of mast cell and basophils and lead to production of mediators of anaphylaxis (see, e.g., Stadler et al., 1993, Int. Arch. Allergy and Immunology 102:121-126). Therefore, a need remains for vaccines for the treatment of IgE-mediated allergic reactions, which do not induce anaphylactic antibodies.

The significant concern over induction of anaphylaxis has resulted in the development of another approach to the treatment of type I allergic disorders consisting of mimotopes that could induce the production of anti-IgE polyclonal antibodies when administered to animals (see, e.g., Rudolf, et al., 1998, Journal of Immunology 160:3315-3321). Kricek et al. (International Publication No. WO 97/31948) screened phage-displayed peptide libraries with the monoclonal antibody BSWI7 to identify peptide mimotopes that could mimic the conformation of the IgE receptor-binding site. These mimotopes could presumably be used to induce polyclonal antibodies that react with free native IgE, but not with receptor-bound IgE as well as block IgE from binding to its receptor. Kricek et al. disclosed peptide mimotopes that are not homologous to any part of the IgE molecule and are thus different from peptides disclosed in the present invention.

A major obstacle facing the development of an anti-IgE vaccine is the lack of information regarding the precise amino acids representing non-anaphylactogenic IgE determinants that could be safely used to immunize allergic subjects and induce non-anaphylactogenic polyclonal antibodies (i.e., polyclonal anti-IgE antibodies that do not bind to receptor-bound IgE). The peptide compositions of the present invention are selected to be non-anaphylactogenic; i.e., the peptide compositions do not result in production of anti-IgE antibodies that could cause cross-linking of IgE bound to mast cells or basophils. Thus peptides of the present invention have superior safety profile and are differentiated by sequence composition from disclosed vaccines based on full-length C2h-CH3 domains.

The safety and efficacy of therapies intended for treatment of IgE-mediated allergies are usually evaluated in animal models such as mice, rats and dogs. A variety of mouse and rat models have been developed for several types of IgE-mediated allergies such as asthma, atopic dermatitis and food allergies (Xin-Min Li, et al.; J. Allergy Clin. Immunol 1999; 103:206-214, Xui-Min et al.; J. Allergy Clin Immunol., 2001, 107:693-702). Although these models have been useful in evaluation of small molecule-based treatment modalities, they are not suitable for evaluation of vaccine-based treatments. This is because the IgE-derived peptide epitope(s) that are used for development of a vaccine for non-rodent species e.g. dogs, can be significantly different from those of mice and rats. Although naturally occurring canine models of allergies are available (e.g. Ermel R W, et al.; Laboratory Animal Science 1997, 47:40-48), these models take a very long time to develop and only a limited number of animals are available at one time. Furthermore, once these dogs are used for a vaccine trial, they cannot be used for further trials. Although dogs can be experimentally sensitized to allergens such as flea allergens (e.g. McDermott, M J, et al.; Molecular Immunology, 2000; 37:361-375), the limitations discussed above still apply. Thus, an appropriate method to induce high levels of IgE and clinical signs of Type I hypersensitivity in dogs is needed to allow rapid evaluation of vaccines and other therapies for treatment of allergies in the desired target species.

Ricin is a lectin found in castor beans which has been found to enhance IgE production directed against a variety of antigens. For example, administration of ricin in conjunction with an antigen can boost the production of IgE in rats that are inherently low in IgE (e.g. Underwood, S L et al.; Immunology. 1995; 85:256-61, Underwood, S L et al.; Int Arch Allergy Immunol. 1995; 107:119-21 and Diaz-Sanchez D. et. al.; Immunology. 1991; 72:297-303). Several studies have determined that ricin enhances IgE responses by preferentially inhibiting a population of activated CD8+ T lymphocytes. These CD8+ cells are thought to express counter regulatory cytokines (e.g. interferon gamma) that down regulate the Th2 cytokines (IL-4, IL-10, and IL-5) released by CD4+ lymphocytes that provide class-switching signals for B-lymphocytes to express IgE (Noble A, et al.; Immunology 1993, 80:326 and Diaz-Sanchez, D. et. Al.; Immunology. 1993; 78:226-236.). Previous studies also show that IgE responses to bee venom phospholipase A2 were reduced by 90% in rats receiving an adoptive transfer of the immunosuppressive CD8+ T lymphocytes (Diaz-Sanchez et al.; immunology 1993, 78:226-236), Compared to CD4+ cells, this population of regulatory CD8+ T lymphocytes has high affinity receptors for the ricin lectin. Following entry of the lectin into the activated cell, cellular protein synthesis is inhibited resulting in killing of the cell. Rats immunized with antigen and ricin show a dramatic increase in the CD4/CD8 ratio due to a 40% decrease in CD8+ T lymphocytes occurring between 7 and 21 days after immunization ((Diaz-Sanchez et al.; Immunology 1993, 78:226-236).

Thus to facilitate and accelerate the development of allergy models, there is a need as provided in the method of the present invention, for induction of high levels of IgE and concomitant induction of clinical signs of allergies in normal dogs following simultaneous exposure to allergens and ricin. This method utilizes normal dogs, which are readily available, and results in sensitization of the majority of dogs in a relatively short period of time.

SUMMARY OF THE INVENTION

The present invention provides compositions and methods for the use of antigenic peptides derived from the Fc portion of the epsilon heavy chain of an IgE molecule as vaccines for the treatment and prevention of IgE-mediated allergic disorders. In particular, the invention provides compositions for the treatment and prevention of IgE-mediated allergic disorders comprising an immunogenic amount of one or more antigenic peptides derived from the CH3 domain of an IgE molecule.

Preferably, compositions of the present invention comprise an immunogenic amount of one or more antigenic peptides comprising the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7. FIGS. 3-9 depict such dog CH3/CH4 peptide sequences. Further preferred compositions of the present invention comprise an immunogenic amount of one or more antigenic peptides comprising the amino acid sequence of SEQ ID NO: 8, SEQ ID NO: 9, SEQ ID NO: 10, SEQ ID NO: 11, SEQ ID NO: 12, SEQ ID NO: 13, or SEQ ID NO: 14. FIGS. 10-16 depict such human CH3/CH4 peptide sequences.

The antigenic peptides can be supplied by direct administration or indirectly as "pro-drugs" using somatic cell gene therapy.

The present invention also provides pharmaceutical compositions comprising an immunogenically effective amount of one or more antigenic peptides derived from the CH3 domain of an IgE molecule and one or more pharmaceutically acceptable carriers. In one embodiment, a pharmaceutical composition of the invention comprises an immunogenically effective amount of one or more antigenic peptides derived from the CH3 domain of an IgE molecule and one or more pharmaceutically acceptable carriers. In another embodiment, a pharmaceutical composition of the invention comprises an immunogenically effective amount of one or more antigenic peptides derived from the junction of the CH3 and CH4 domains of an IgE molecule and one or more pharmaceutically acceptable carriers.

In a particular embodiment, a pharmaceutical composition of the invention comprises one or more pharmaceutical carriers and an immunogenically effective amount of one or more antigenic fusion proteins comprising an antigenic peptide derived from the CH3 domain of an IgE molecule and a heterologous carrier protein. In another particular embodiment, a pharmaceutical composition of the invention comprises one or more pharmaceutical carriers and an immunogenically effective amount of one or more antigenic fusion proteins comprising an antigenic peptide derived from the junction of the CH3 and CH4 domains of an IgE molecule and a heterologous carrier protein.

In a preferred embodiment, a pharmaceutical composition of the invention comprises one or more pharmaceutical carriers and an immunogenically effective amount of one or more antigenic peptides comprising the amino acid sequence of SEQ ID NO: 1, SEQ ID NO: 2, SEQ ID NO: 3, SEQ ID NO: 4, SEQ ID NO: 5, SEQ ID NO: 6, or SEQ ID NO: 7. In another preferred embodiment, a pharmaceutical composition of the present invention comprises one or more pharmaceutical carriers and an antigenic fusion protein comprising the amino acid sequence of SEQ ID NO: 1, SEQ ID NO: 2, SEQ ID NO:, SEQ ID NO: 4, SEQ ID NO: 5, SEQ ID NO: 6, or SEQ ID NO: 7 coupled to a heterologous carrier protein.

In a further preferred embodiment, a pharmaceutical composition of the invention comprises one or more pharmaceutical carriers and an immunogenically effective amount of one or more antigenic peptides comprising the amino acid sequence of SEQ ID NO: 8, SEQ ID NO: 9, SEQ ID NO: 10, SEQ ID NO: 11, SEQ ID NO: 12, SEQ ID NO: 13, or SEQ ID NO: 14. In another preferred embodiment, a pharmaceutical composition of the present invention comprises one or more pharmaceutical carriers and an antigenic fusion protein comprising the amino acid sequence of SEQ NO: 8, SEQ ID NO: 9, SEQ ID NO: 10, SEQ ID NO: 11, SEQ ID NO: 12, SEQ ID NO: 13, or SEQ ID NO: 14 coupled to a heterologous carrier protein.

The present invention also provides pharmaceutical compositions comprising an immunogenically effective amount of one or more antigenic peptides derived from the CH3 domain of an IgE molecule, a pharmaceutically acceptable carrier, and an adjuvant. Adjuvants encompass any compound capable of enhancing an immune response to an antigen. Examples of adjuvants which may be effective, include, but are not limited to: aluminum hydroxide, monophosphoryl lipid A (MPLA)-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1"-2"-dipalmitoyl-sn-glycero-3-hydroxyphosphoryloxy)-ethylamine, simple immunostimulatory oligonucleotides, cytokines such as IL-12, IL-2 or IL-1, saponins, and microbial toxins such as cholera toxin, heat labile toxin and genetically altered derivatives of them.

In one embodiment, a pharmaceutical composition of the invention comprises an immunogenically effective amount of one or more antigenic peptides derived from the CH3 domain of an IgE molecule, a pharmaceutically acceptable carrier, and an adjuvant. In another embodiment, a pharmaceutical composition of the invention comprises an immunogenically effective amount of one or more antigenic peptides derived from the junction of the CH3 and CH4 domains of an IgE molecule, a pharmaceutically acceptable carrier, and an adjuvant. In another embodiment, a pharmaceutical composition of the invention comprises a pharmaceutical carrier, an adjuvant and an immunogenically effective amount of one or more antigenic fusion proteins comprising an antigenic peptide derived from the CH3 domain of an IgE molecule and a heterologous carrier protein. In yet another embodiment, a pharmaceutical composition of the invention comprises a pharmaceutical carrier, an adjuvant and an immunogenically effective amount of one or more antigenic fusion proteins comprising an antigenic peptide derived from the junction of the CH3 and CH4 domains of an IgE molecule and a heterologous carrier protein.

In a preferred embodiment, a pharmaceutical composition of the invention comprises a pharmaceutical carrier, an adjuvant and an immunogenically effective amount of one or more antigenic peptides comprising of the amino acid sequence of SEQ ID NO: 1, SEQ ID NO: 2, SEQ ID NO: 3, SEQ ID NO: 4, SEQ ID NO: 5, SEQ ID NO: 6, or SEQ ID NO: 7. In another preferred embodiment, a pharmaceutical composition of the present invention comprises a pharmaceutical carrier, an adjuvant, and an immunogenically effective amount of one or more antigenic fusion proteins comprising the amino acid sequence of SEQ ID NO: 1, SEQ ID NO 2, SEQ ID NO: 3, SEQ ID NO: 4, SEQ ID NO: 5, SEQ ID NO: 6 or SEQ ID NO: 7 coupled to a heterologous carrier protein.

In a further preferred embodiment, a pharmaceutical composition of the invention comprises a pharmaceutical carrier, an adjuvant and an immunogenically effective amount of one or more antigenic peptides comprising of the amino acid sequence of SEQ ID NO: 8, SEQ ID NO: 9, SEQ ID NO: 10, SEQ ID NO: 11, SEQ ID NO: 12, SEQ ID NO: 13, or SEQ ID NO: 14. In yet another preferred embodiment, a pharmaceutical composition of the present invention comprises a pharmaceutical carrier, an adjuvant, and an immunogenically effective amount of one or more antigenic fusion proteins comprising the amino acid sequence of SEQ ID NO: 8, SEQ ID NO 9, SEQ ID NO: 10, SEQ ID NO: 11, SEQ ID NO: 12, SEQ ID NO: 13 or SEQ ID NO: 14 coupled to a heterologous carrier protein.

The present invention also provides methods of administering compositions of the invention to animals, preferably mammals and most preferably humans for the treatment or prevention of IgE-mediated allergic disorders. The compositions of the present invention are in suitable formulation to be administered to animals, preferably mammals such as companion animals (e.g., dogs, cats, and horses) and livestock (e.g., cows and pigs), and most preferably humans. The compositions of the invention are administered in an amount effective to elicit an immune response, for example, the production of polyclonal antibodies with specificity for an IgE molecule. In one embodiment, the compositions of the invention are administered in an amount effective to induce the production of polyclonal antibodies with specificity for the Fc portion of an IgE molecule required for IgE to bind to its receptor (i.e., the CH3 domain of an IgE molecule). In a preferred embodiment, the compositions of present invention are administered in an amount effective to induce the production of anti-IgE antibodies which bind to soluble (free) IgE in serum and other bodily fluids, prevent IgE from binding to its high affinity receptors on mast cells and basophils, and do not cross-link receptor-bound IgE. Accordingly, the compositions of the invention are administered in an amount effective to induce the production of polyclonal antibodies which do not induce anaphylaxis for the treatment or prevention of IgE-mediated allergic disorders.

The present invention also provides a method for evaluating the effect of anti-IgE vaccines in dogs which comprises sensitization of the dogs to an allergen by concurrent administration of the allergen and ricin in amounts sufficient to induce hypersensitivity in the dogs, followed by challenge with the allergen and observation of the resulting sensitivity of the dogs to the challenge allergen. Specific embodiments of the method include those wherein the allergen is a flea allergen or a food allergen such as an ascaris allergen. In one embodiment of the method the hypersensitivity is type I hypersensitivity, In another embodiment of the method sensitization results in higher levels of IgE in the hypersensitized dogs than found in non-hypersensitized dogs.

The present invention further provides a method for inducing high levels of IgE and clinical signs of hypersensitivity in dogs for evaluating the effect of anti-IgE vaccines in the dogs which comprises: sensitization of the dogs to an allergen sufficient to induce hypersensitivity in the dogs by concurrent administration of amounts of the allergen and ricin sufficient to the dogs, followed by challenge with the allergen and observation of the resulting sensitivity of the dogs to the challenge allergen.

BRIEF DESCRIPTION OF THE FIGURES

FIG. 1 depicts the ELISA reactivity of sera obtained from rabbits immunized with RBS peptides 1-4 (SEQ ID 1-4; respectively) against the respective RBS peptides coated onto neutravidin plates.

FIG. 2 depicts the ELISA reactivity of sera obtained from rabbits immunized with RBS peptides 1-4 (SEQ ID 1-4, respectively) against the full-length canine IgE protein.

FIGS. 3-9 depict dog CH3/CH4 peptide sequences.

FIG. 3 depicts SEQ ID NO: 1; Dog CH3/CH4 peptide sequence.

FIG. 4 depicts SEQ ID NO: 2; Dog CH3/CH4 peptide sequence.

FIG. 5 depicts SEQ ID NO: 3; Dog CH3/CH4 peptide sequence.

FIG. 6 depicts SEQ ID NO: 4; Dog CH3/CH4 peptide sequence.

FIG. 7 depicts SEQ ID NO: 5; Dog CH3/CH4 peptide sequence.

FIG. 8 depicts SEQ ID NO: 6; Dog CH3/CH4 peptide sequence.

FIG. 9 depicts SEQ 10 NO: 7; Dog CH3/CH4 peptide sequence.

FIGS. 10-16 depict human CH3/CH4 peptide sequences.

FIG. 10 depicts SEQ ID NO: 8; human CH3/CH4 peptide sequence.

FIG. 11 depicts SEQ ID NO: 9; human CH3/CH4 peptide sequence.

FIG. 12 depicts SEQ ID NO: 10; human CH3/CH4 peptide sequence.

FIG. 13 depicts SEQ ID NO: 11; human CH3/CH4 peptide sequence.

FIG. 14 depicts SEQ ID NO: 12; human CH3/CH4 peptide sequence.

FIG. 15 depicts SEQ ID NO: 13; human CH3/CH4 peptide sequence.

FIG. 16 depicts SEQ ID NO: 14; human CH3/CH4 peptide sequence.

FIG. 17 depicts SEQ ID NO: 15; Dog CH3/CH4 nucleotide sequence.

FIG. 18 depicts SEQ ID NO: 16; Dog CH3/CH4 nucleotide sequence.

FIG. 19 depicts SEQ ID NO: 17; Dog CH3/CH4 nucleotide sequence.

FIG. 20 depicts SEQ ID NO: 18; Dog CH3/CH4 nucleotide sequence.

FIG. 21 depicts SEQ ID NO: 19; Dog CH3/CH4 nucleotide sequence.

FIG. 22 depicts SEQ ID NO: 20; Dog CH3/CH4 nucleotide sequence.

FIG. 23 depicts SEQ ID NO: 21; Dog CH3/CH4 nucleotide sequence.

FIG. 24 depicts SEQ ID NO: 22; Dog CH3/CH4 nucleotide sequence.

FIG. 25 depicts SEQ ID NO: 23; Dog CH3/CH4 nucleotide sequence.

FIG. 26 depicts SEQ ID NO: 24; Dog CH3/CH4 nucleotide sequence.

FIG. 27 depicts SEQ ID NO: 25; Dog CH3/CH4 nucleotide sequence.

FIG. 28 depicts SEQ ID NO: 26; Dog CH3/CH4 nucleotide sequence.

FIG. 29 depicts SEQ ID NO: 27; Dog CH3/CH4 nucleotide sequence.

FIG. 30 depicts SEQ ID NO: 28; Dog CH3/CH4 nucleotide sequence.

DETAILED DESCRIPTION OF THE INVENTION

The present invention provides compositions and methods for the use of antigenic peptides derived from the Fc portion of the epsilon heavy chain of an IgE molecule as vaccines for the treatment and prevention of IgE-mediated allergic disorders. In particular, the present invention provides compositions comprising an immunogenic amount of an antigenic peptide derived from the CH3 domain of an IgE molecule effective for treatment or prevention of an IgE-mediated allergic disorder. Preferably, compositions of the present invention comprise an immunogenic amount of one or more antigenic peptides comprising the amino acid sequence of SEQ ID NO: 1, SEQ ID NO: 2, SEQ ID NO: 3, or SEQ ID NO: 4, SEQ ID NO; 5, SEQ ID NO: 6, or SEQ ID NO: 7 (FIGS. 3-9). Further preferred compositions of the present invention comprise an immunogenic amount of one or more antigenic peptides comprising the amino acid sequence of SEQ ID NO: 8, SEQ ID NO: 9, SEQ ID NO: 0, or SEQ ID NO: 11, SEQ. ID NO: 12, SEQ ID NO: 13, or SEQ ID NO:14 (FIGS. 10-16).

The antigenic peptides of the present invention comprise an amino acid sequence of the CH3 domain of an IgE molecule or a fragment thereof and induce the production of anti-IgE antibodies, which are not anaphylactic. The present invention also encompasses antigenic peptides comprising an amino acid sequence of the junction of the CH3 and CH4 domains of an IgE molecule, which induce anti-IgE antibodies that are not anaphylactic. In particular, the antigenic peptides of the present invention induce the production of anti-IgE antibodies which bind to soluble (free) IgE in serum and other bodily fluids, prevent IgE from binding to its high affinity receptors on mast cells and basophils, and do not cross-link receptor-bound IgE. The antigenic peptides of the present invention may be coupled to one or more heterologous peptides. The antigenic peptides of the invention can be supplied by direct administration or indirectly as "pro-drugs" using somatic cell gene therapy.

In one embodiment, an antigenic peptide of the invention comprises the entire CH3 domain of an IgE molecule of any species. In another embodiment, an antigenic peptide of the invention comprises a fragment of the CH3 domain of an IgE molecule of any species, wherein the fragment is at least five amino acid residues long, preferably at least 10 amino acid residues long, more preferably at least 15 amino acid residues long, at least 20 amino acid residues long, at least 25 amino acid residue long, or at least 30 amino acid residues long. In a preferred embodiment, an antigenic peptide of the invention comprises an amino acid sequence of a fragment of the CH3 domain of an IgE molecule that is between 28 and 31 amino acid residues. In another preferred embodiment, an antigenic peptide of the present invention comprises an amino acid sequence of a fragment of the CH3 domain of an IgE molecule that does not possess two cysteine amino acid residues separated by 21 amino acid residues, 22 amino acid residues, 23 amino acid residues, 24 amino acid residues, or 25 amino acid residues. In a specific embodiment, an antigenic peptide of the invention comprises the junction of the CH3 and CH4 domains of an IgE molecule or a fragment thereof, wherein the fragment is at least five amino acid residues long, preferably at least 10 amino acid residues long, more preferably at least 15 amino acid residues long, at least 20 amino acid residues long, at least 25 amino acid residue long, or at least 30 amino acid residues long.

In a preferred embodiment, an antigenic peptide of the present invention comprises the amino acid sequence of SEQ ID NO: 1, SEQ ID NO: 2, SEQ ID NO: 3, SEQ ID NO: 4, SEQ ID NO: 5, SEQ ID NO: 6, or SEQ ID NO: 7 (FIGS. 3-9) In another preferred embodiment, an antigenic peptide of the invention comprises the amino acid sequence of SEQ ID NO: 8, SEQ ID NO: 9, SEQ ID NO: 10, SEQ ID NO: 11, SEQ ID NO: 12, SEQ ID NO: 13, or SEQ ID NO: 14 (FIGS. 10-16).

The present invention also provides antigenic fusion proteins comprising an antigenic peptide and a heterologous carrier protein. In a specific embodiment, an antigenic fusion protein comprises the entire CH3 domain of an IgE molecule and a heterologous carrier protein. In another specific embodiment, an antigenic fusion protein comprises a fragment of an IgE molecule coupled to a heterologous carrier protein, wherein the fragment of the CH3 domain is at least five amino acids long, preferably at least 10 amino acid residues long, more preferably at least 15 amino acid residues long, at least 20 amino acid residues long, at least 25 amino acid residue long, or at least 30 amino acid residues long. In another embodiment, an antigenic fusion protein of the present invention comprises the junction of the CH3 and CH4 domains of an IgE molecule or a fragment thereof coupled to a heterologous carrier protein. In a preferred embodiment, an antigenic fusion protein of the present invention comprises the amino acid sequence of SEQ ID NO: 1, SEQ ID NO: 2, SEQ ID NO: 3, SEQ ID NO: 4, SEQ ID NO: 5, SEQ ID NO: 6, or SEQ ID NO: 7. In another preferred embodiment, an antigenic fusion protein of the present invention comprises the amino acid sequence of SEQ ID NO: 8, SEQ ID NO: 9, SEQ ID NO: 10, SEQ ID NO: 11, SEQ ID NO: 12, SEQ ID NO: 13, or SEQ ID NO: 14.

The present invention also provides antigenic peptides or antigenic fusion proteins comprising an amino acid sequence derived from a CH3 domain of an IgE molecule in which one or more amino acid substitutions, additions or deletions has been introduced. Mutations can be introduced by standard techniques known to those of skill in the art.

For example, one or more mutations at the nucleotide level which result in one or more amino acid mutations can be introduced by site-directed mutagenesis or PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for their ability to induce anti-IgE antibodies which do not cause anaphylaxis.

The present invention also provides methods for treating or preventing IgE-mediated allergic disorders in animals, preferably mammals and most preferably humans, comprising administering pharmaceutical compositions, which do not induce anaphylaxis. The pharmaceutical compositions to be administered in accordance with the methods of the present invention encompass antigenic peptides derived from the CH3 domain of IgE molecule. The pharmaceutical compositions to be administered in accordance with the methods of the present invention also include: (i) recombinant antigenic peptides comprising an amino acid sequence of a CH3 domain of an IgE molecule or a fragment thereof; (ii) recombinant antigenic fusion proteins comprising an amino acid sequence of a CH3 domain of an IgE molecule or a fragment thereof and a heterologous carrier protein; (iii) recombinant antigenic peptides comprising an amino acid sequence of a junction of the CH3 and CH4 domains of an IgE molecule or a fragment thereof; (iv) recombinant antigenic fusion proteins comprising an amino acid sequence of a junction of the CH3 and CH4 domains of an IgE molecule or a fragment thereof: (v) plasmid compositions comprising polynucleotides encoding an antigenic peptide having an amino acid sequence of a CH3 domain of an IgE molecule or a fragment thereof; (vi) plasmid compositions comprising polynucleotides encoding for antigenic fusion proteins comprising an amino acid sequence of a CH3 domain of an IgE molecule or a fragment thereof and a heterologous carrier protein; (vii) plasmid compositions comprising polynucleotides encoding an antigenic peptide having an amino acid sequence of a junction of the CH3 and CH4 domains of an IgE molecule or a fragment thereof; and (viii) plasmid compositions comprising polynucleotides encoding for antigenic fusion proteins comprising an amino acid sequence of a junction of the CH3 and CH4 domains of an IgE molecule or a fragment thereof.

In one embodiment, a pharmaceutical composition of the present invention comprises one or more antigenic peptides comprising the amino acid sequence of the entire CH3 domain of an IgE molecule. In another embodiment, a pharmaceutical composition of the present invention comprises one or more antigenic peptides comprising the amino acid sequence of a fragment of the CH3 domain of an IgE molecule, wherein the fragment is at least five amino acid residues long, preferably at least 10 amino acid residues long, more preferably at least 15 amino acid residues long, at least 20 amino acid residues long, at least 25 amino acid residue long, or at least 30 amino acid residues long. In a preferred embodiment, a pharmaceutical composition of the present invention comprises one or more antigenic peptides comprising the amino acid sequence of a fragment of the CH3 domain of an IgE molecule that is between 28 and 31 amino acid residues. In another preferred embodiment, pharmaceutical compositions of the present invention comprise one or more antigenic peptides comprising the amino acid sequence of a fragment of the CH3 domain of an IgE molecule that does not possess two cysteine amino acid residues separated by 21 amino acid residues, 22 amino acid residues, 23 amino acid residues, 24 amino acid residues, or 25 amino acid residues. In accordance with these embodiments, the pharmaceutical compositions may further comprise an adjuvant.

In a specific embodiment, a pharmaceutical composition of the present invention comprises one or more antigenic peptides comprising the amino acid sequence of a junction of the CH3 and CH4 domains of an IgE molecule or a fragment thereof. In accordance with this embodiment, the pharmaceutical composition may further comprise an adjuvant. Preferably, the antigenic peptide comprising the amino acid sequence of a junction of the CH3 and CH4 domains of an IgE molecule or a fragment thereof is between 28 and 31 amino acid residues.

The present invention also provides pharmaceutical compositions comprising one or more antigenic fusion proteins.

In a specific embodiment, a pharmaceutical composition of the present invention comprises one or more antigenic fusion proteins comprising an antigenic peptide of the invention and a heterologous carrier protein. In accordance with this embodiment, the pharmaceutical composition may further comprise an adjuvant.

As used herein the term "heterologous carrier protein" refers to a protein which does not possess high homology to a protein found in the species that is receiving a composition of the invention and elicits an immune response. A protein possesses high homology if it is at least 75% identical, more preferably at least 85% identical or at least 90% identical to a protein as determined by any known mathematical algorithm utilized for the comparison of two amino acid sequences (see, e.g., Karlin and Altschul, 1990, Proc. Natl. Acad. Sci. USA 87: 2264-2268; Karlin and Altschul, 1993, Proc. Natl. Acad. Sci. USA 90: 5873-5877; Torellis and Robotti, 1994, Comput. Appl. Biosci. 10: 3-5; and Pearson and Lipman, 1988, Proc. Natl. Acad. Sci. 85: 2444-8). Preferably, the percent identity of two amino acid sequences is determined by BLAST protein searches with the XBLAST program, score=50, wordlength=3. Examples of heterologous carrier proteins include, but are not limited to, KLh, PhoE, rmLT, TraT, or gD from BhV-1 virus.

A heterologous carrier protein can be fused to the N-terminus or C-terminus of an antigenic peptide of the invention. Antigenic fusion proteins of the invention can be produced by techniques known to those of skill in the art, for example, by standard recombinant DNA techniques. For example, a nucleotide sequence encoding an antigenic fusion protein can be synthesized by conventional techniques including automated DNA synthesizers. Alternatively, PCR amplification of nucleotide fragments can be carried out using anchor primers which give rise to complementary overhangs between two consecutive nucleotide fragments which can subsequently be annealed and reamplified to generate a nucleotide sequence encoding an antigenic fusion protein (see, e.g., Ausubel et al., infra). Moreover, many expression vectors are commercially available that already encode a fusion moiety (e.g., a GST polypeptide). A nucleic acid encoding an antigenic peptide of the invention can be cloned into such an expression vector such that the fusion moiety is linked in-frame to the antigenic peptide of the invention. Further, a heterologous carrier protein can be fused to an antigenic peptide by chemical methods known to those of skill in the art.

In a specific embodiment, a pharmaceutical composition of the present invention provides an antigenic peptide having an amino acid sequence comprising amino acid residues of SEQ ID NO: 1, SEQ ID NO: 2, SEQ ID NO: 3, SEQ ID NO: 4, SEQ ID NO: 5, SEQ ID NO: 6, or SEQ ID NO: 7. In another embodiment, a pharmaceutical composition of the present invention provides an antigenic fusion protein comprising the amino acid sequence of SEQ ID NO: 1 coupled to a heterologous carrier protein, the amino acid sequence of SEQ ID NO: 2 coupled to a heterologous carrier protein, the amino acid sequence of SEQ ID NO: 3 coupled to a heterologous carrier protein, the amino acid sequence of SEQ ID NO: 4 coupled to a heterologous carrier protein, the amino acid sequence of SEQ ID NO: 5 coupled to a heterologous carrier protein, the amino acid sequence of SEQ ID NO: 6 coupled to a heterologous carrier protein, or the amino acid sequence of SEQ ID NO: 7 coupled to a heterologous carrier protein. In another specific embodiment, a pharmaceutical composition of the present invention provides an antigenic fusion protein having the amino acid sequence of SEQ ID NO: 8, SEQ ID NO: 9, SEQ ID NO: 10, SEQ ID NO: 11, SEQ ID NO: 12, SEQ ID NO: 13, or SEQ ID NO: 14. In another embodiment, a pharmaceutical composition of the present invention provides an antigenic fusion protein comprising the amino acid sequence of SEQ ID NO: 8 coupled to a heterologous carrier protein, the amino acid sequence of SEQ ID NO: 9 coupled to a heterologous carrier protein, the amino acid sequence of SEQ ID NO: 10 coupled to a heterologous carrier protein, the amino acid sequence of SEQ ID NO: 11 coupled to a heterologous carrier protein, the amino acid sequence of SEQ ID NO: 12 coupled to a heterologous carrier protein, the amino acid sequence of SEQ ID NO: 13 coupled to a heterologous carrier protein, or the amino acid sequence of SEQ ID NO: 14 coupled to a heterologous carrier protein. In accordance with these embodiments, the pharmaceutical compositions may further comprise an adjuvant.

The pharmaceutical compositions of the present invention are in suitable formulation to be administered to animals such as companion animals (e.g., dogs and cats) and livestock (e.g., pigs, cows and horses) and humans for the treatment or prevention of IgE-mediated allergic disorders. Preferably, a pharmaceutical composition of the invention comprises an antigenic peptide derived from the CH3 domain of the IgE molecule of the same species receiving the antigenic peptide to treat or prevent an IgE-mediated allergic disorder. IgE-mediated allergic disorders include, but are not limited to, asthma, allergic rhinitis, gastrointestinal allergies such as food allergies, eosinophilia, conjunctivitis, glomerular nephritis and graft-versus-host disease. The pharmaceutical compositions of the invention are administered to a subject (an animal) in an amount effective for the treatment, prevention or inhibition of IgE-mediated allergic disorders, or an amount effective for inducing an anti-IgE immune response the production of anti-IgE polyclonal antibodies) that is not anaphylactic, or an amount effective for inhibiting or reducing the release of vasoactive substances such as histamine, or an amount effective for alleviating one or more symptoms associated with an IgE-mediated allergic disorder.

The pharmaceutical compositions of the invention can be used with any known method of treating IgE-mediated allergic disorders. In one embodiment, one or more pharmaceutical compositions of the invention and one or more antihistamines are administered to an animal for the treatment or prevention of an IgE-mediated allergic disorder. In another embodiment, one or more pharmaceutical compositions of the invention and one or more corticosteroids are administered to an animal for the treatment or prevention of an IgE-mediated allergic disorder. In yet another embodiment, one or more pharmaceutical compositions of the invention and one or more anti-IgE monoclonal antibodies (e.g., BSW17) are administered to an animal for the treatment or prevention of an IgE-mediated allergic disorder.

The present invention also comprises polynucleotide sequences encoding the antigenic peptides or antigenic fusion proteins of the invention. The present invention comprises nucleic acid molecules comprising different polynucleotide sequences due to the degeneracy of the genetic code which encode identical antigenic peptides and antigenic fusion proteins. The present invention encompasses antigenic peptides comprising an amino acid sequence of a CH3 domain of an IgE molecule or a fragment thereof encoded by the polynucleotide sequence of any species. The polynucleotide sequence of a CH3 domain of an IgE molecule can be obtained from scientific literature, Genbank, or using cloning techniques known to those of skill in the art. In particular, the present invention encompasses polynucleotide sequences encoding human and canine the CH3 domain of an IgE molecule the disclosed in Genbank Accession Number AAB59424.1 and AAA56797.1; respectively, are incorporated herein by reference. The present invention further encompasses antigenic peptides comprising an amino acid sequence of a junction of the CH3 and CH4 domains of an IgE molecule or a fragment thereof encoded by the polynucleotide sequence of any species. The polynucleotide sequence of a junction of the CH3 and CH4 domains of an IgE molecule can be obtained from scientific literature, Genbank, or using cloning techniques known to those of skill in the art.

The present invention also encompasses antigenic fusion proteins comprising an antigenic peptide encoded by a polynucleotide sequence of any species and a heterologous carrier protein encoded by a polynucleotide sequence of a different species from the antigenic peptide. The polynucleotide sequence of a heterologous carrier protein can be obtained from scientific literature, Genbank, or using cloning techniques known to those of skill in the art.

The polynucleotide sequence encoding an antigenic peptide or an antigenic fusion protein of the invention can be inserted into an appropriate expression vector, i.e., a vector which contains the necessary elements for the transcription and translation of the inserted protein-coding sequence. The necessary transcriptional and translational signals can also be supplied by the native IgE genes or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing polynucleotides encoding antigenic peptides or antigenic fusion proteins, and appropriate transcriptional and translational control signals. These methods may include in vitro recombinant DNA and synthetic techniques and in vivo recombinants (genetic recombination), Expression of the nucleic acid sequence encoding an antigenic peptide or an antigenic fusion protein of the invention may be regulated by a second nucleic acid sequence so that the antigenic peptide or the antigenic fusion protein is expressed in a host transformed with the recombinant DNA molecule. For example, expression of an antigenic peptide or an antigenic fusion protein of the invention may be controlled by any promoter or enhancer element known in the art. Promoters which may be used to control the expression of an antigenic peptide or an antigenic fusion protein of the invention include, but are not limited to, the Cytomeglovirus (CMV) immediate early promoter region, the SV40 early promoter region (Bernoist and Chambon, 1981, Nature 290: 304-310), the promoter contained in the 3" long terminal repeat of Rous sarcoma virus (Yamamoto, et al., 1980, Cell 22: 787-797), the herpes thymidine kinase promoter (Wagner et al., 1981, Proc. Natl. Acad. Sci. USA 78: 1441-1445), the regulatory sequences of the metallothionein gene (Brinster at al., 1982, Nature 296: 39-42); prokaryotic expression vectors such as the β-lactamase promoter (VIIIa-Kamaroff et al., 1978, Proc. Natl. Acad. Sci. USA 75: 3727-3731), or the tac promoter (DeBoer at al., 1983, Proc. Natl. Acad. Sci. USA 80: 21-25); see also "Useful proteins from recombinant bacteria" in Scientific American, 1980, 242: 74-94; plant expression vectors comprising the nopaline synthetase promoter region (herrera-Estrella at al., Nature 303: 209-213) or the cauliflower mosaic virus 35S RNA promoter (Gardner et al., 1981, Nucl. Acids Res. 9: 2871), and the promoter of the photosynthetic enzyme ribulose biphosphate carboxylase (herrera-Estrella et al., 1984, Nature 310: 115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al. 1984, Cell 38: 639-646; Ornitz et al., 1986, Cold Spring harbor Symp. Quant. Biol. 50: 399-409; MacDonald, 1987, hepatology 7:425-515); insulin gene control region which is active in pancreatic beta cells (hanahan, 1985, Nature 315: 115-122); immunoglobulin gene control region which is active in lymphoid cells (Grosschedl et al., 1984, Cell 38: 647-658; Adames et al., 1985, Nature 318: 533-538; and Alexander et al., 1987, Mol. Cell. Biol. 7: 1436-1444); mouse mammary tumor virus control region which is active in testicular, breast, lymphoid and mast cells (Leder et al., 1986, Cell 45: 485-495); albumin gene control region which is active in liver (Pinkert et al., 1987, Genes and Devel. 1: 268-276); alpha-fetoprotein gene control region which is active in liver (Krumlauf et al 1985, Mol. Cell. Biol. 5: 1639-1648; and hammer et al., 1987, Science 235: 53-58); alpha 1-antitrypsin gene control region which is active in the liver (Kelsey et al., 1987, Genes and Devel. 1: 161-171); beta-globin gene control region which is active in myeloid cells (Mogram et al., 1985, Nature 315: 338-340; and Kollias et al., 1986, Cell 46: 89-94); myelin basic protein gene control region which is active in oligodendrocyte cells in the brain (Readhead et al., 1987, Cell 48: 703-712); myosin light chain-2 gene control region which is active in skeletal muscle (Sani, 1985, Nature 314: 283-286); swine alpha-skeletal actin control region which is active in muscle (Reecy, M. et al., 1998, Animal Biotechnology 9: 101-120); and gonadotropic releasing hormone gene control region which is active in the hypothalamus (Mason et al 1986, Science 234: 1372-1378).

In a specific embodiment, a vector is used that comprises a promoter operably linked to an antigenic peptide-encoding nucleic acid, one or more origins of replication, and, optionally, one or more selectable markers (e.g., an antibiotic resistance gene). In another specific embodiment, a vector is used that comprises a promoter operably linked to an antigenic fusion protein-encoding nucleic acid, one or more origins of replication, and, optionally, one or more selectable markers (e.g., an antibiotic resistance gene).

Expression vectors containing gene inserts can be identified by three general approaches: (a) nucleic acid hybridization; (b) presence or absence of "marker" gene functions; and (c) expression of inserted sequences. In the first approach, the presence of antigenic peptide-encoding polynucleotides or antigenic fusion protein-encoding polynucleotides inserted in an expression vector(s) can be detected by nucleic acid hybridization using probes comprising sequences that are homologous to the inserted polynucleotide sequence. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of the gene(s) in the vector(s). For example, if a nucleic acid molecule encoding an antigenic peptide or an antigenic fusion protein is inserted within the marker gene sequence of the vector, recombinants containing the nucleic acid molecule encoding the antigenic peptide or the antigenic fusion protein insert can be identified by the absence of the marker gene function. In the third approach, recombinant expression vectors can be identified by assaying the gene product expressed by the recombinant. Such assays can be based, for example, on the physical or functional properties of an antigenic peptide or an antigenic fusion protein in in vitro assay systems, e.g., binding of an antigenic peptide or an antigenic fusion protein with an anti-IgE antibody.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

The term "host cell" as used herein refers not only to the particular subject cell into which a recombinant DNA molecule is introduced but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell strain may be chosen which modulates the expression of the inserted sequences, or modifies and processes the gene product in the specific fashion desired. Expression from certain promoters can be elevated in the presence of certain inducers; thus, expression of the genetically engineered may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of an antigenic peptide or antigenic fusion protein of the invention. Furthermore, different vector/host expression systems may effect processing reactions to different extents.

For long-term, high-yield production of recombinant proteins, stable expression is preferred. For example, cell lines which stably express an antigenic peptide or an antigenic fusion protein of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express an antigenic peptide or an antigenic protein of the invention, Such engineered cell lines may be particularly useful in the screening and evaluation of anti-IgE antibodies or other agents (e.g., organic molecules, inorganic molecules, organic/inorganic complexes, polypeptides, peptides, peptide mimics, polysaccharides, saccharides, glycoproteins, nucleic acids, DNA and RNA strands and oligonucleotides, etc.) that affect binding of an IgE molecule to its receptor.

A number of selection systems may be used, including but not limited to the herpes simplex virus thymidine kinase (Wigler et al., 1977, Cell 11: 223), hypoxanthine-guanine phosphoribosyltransferase (Szybalska & Szybalski, 1962, Proc. Natl. Acad. Sci. USA 48: 2026), and adenine phosphoribosyltransferase (Lowy et al., 1980, Cell 22: 817) genes can be employed in $tk^+$, $hgprt^-$ or $aprt^-$ cells, respectively. Also, antimetabolite resistance can be used as the basis of selection for dhfr, which confers resistance to methotrexate (Wigler at al., 1980, Proc. Natl. Acad. Sci. USA 77: 3567; O'hare at al., 1981, Proc. Natl. Acad. Sci. USA 78: 1527); gpt, which confers resistance to mycophenofic acid (Mulligan & Berg, 1981, Proc. Natl. Acad. Sci. USA 78: 2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30: 147) genes.

In a specific embodiment, one or more nucleic acid molecules comprising a polynucleotide sequence encoding an antigenic peptide of the invention, are administered to treat or prevent IgE-mediated allergic disorders, by way of gene therapy. In another specific embodiment, one or more nucleic acid molecules comprising a polynucleotide sequence encoding an antigenic fusion protein, are administered to treat or prevent IgE-mediated allergic disorders, by way of gene therapy. In yet another specific embodiment, one or more nucleic acid molecules comprising a polynucleotide sequence encoding an antigenic peptide of the invention, and one or more nucleic acid molecules comprising a polynucleotide sequence encoding an antigenic fusion protein of the invention are administered to treat or prevent IgE-mediated allergic disorders, by way of gene therapy. Gene therapy refers to therapy performed by the administration to a subject of an expressed or expressible nucleic acid. In this embodiment of the invention, the nucleic acids produce their encoded antigenic peptides or antigenic fusion proteins that mediate a therapeutic effect by eliciting an immune response such as the production of anti-IgE antibodies.

Any of the methods for gene therapy available in the art can be used according to the present invention. Exemplary methods are described below.

For general reviews of the methods of gene therapy, see Goldspiel et al., 1993, Clinical Pharmacy 12: 488-505; Wu and Wu, 1991, Biotherapy 3: 87-95; Tolstoshev, 1993, Ann. Rev. Pharmacol. Toxicol. 32: 573-596; Mulligan, 1993, Science 260: 926-932; and Morgan and Anderson, 1993, Ann. Rev. Biochem. 62: 191-217; May, 1993, TIBTECh 11(5): 155-215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, a pharmaceutical composition comprises nucleic acid sequences encoding an antigenic peptide of the invention, said nucleic acid sequences being part of expression vectors that express the antigenic peptide in a suitable host. In particular, such nucleic acid sequences have promoters operably linked to the antigenic peptide coding regions, said promoters being inducible or constitutive, and, optionally, tissue-specific. In another preferred aspect, a pharmaceutical composition comprises nucleic acid sequences encoding an antigenic fusion protein of the invention, said nucleic acid sequences being part of expression vectors that express the antigenic fusion protein in a suitable host. In particular, such nucleic acid sequences have promoters operably linked to the antigenic fusion protein coding regions, said promoters being inducible or constitutive, and, optionally, tissue-specific. In another particular embodiment, nucleic acid molecules are used in which the coding sequences of an antigenic peptide of the invention and any other desired sequences are flanked by regions that promote homologous recombination at a desired site in the genome, thus providing for intrachromosomal expression of the nucleic acids encoding the antigenic peptide (Koller and Smithies, 1989, Proc. Natl. Acad. Sci. USA 86:8932-8935; and Zillstra et al., 1989, Nature 342:435-438). In another particular embodiment, nucleic acid molecules are used in which the coding sequences of an antigenic fusion protein of the invention and any other desired sequences are flanked by regions that promote homologous recombination at a desired site in the genome, thus providing for intrachromosomal expression of the nucleic acids encoding the antigenic protein.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular. e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262: 4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22636 dated Dec. 23, 1992 (Wilson et al.); WO92/20316 dated Nov. 26, 1992 (Findeis et al.); WO93/14188 dated Jul. 22, 1993 (Clarke et al.); and WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86: 8932-8935; Zijistra et al., 1989, Nature 342: 435-438).

In specific embodiments, viral vectors that contain nucleic acid sequences encoding antigenic peptides or antigenic fusion proteins are used. For example, a retroviral vector containing nucleic acid sequences encoding an antigenic peptide or an antigenic fusion protein can be used (see, e.g., Miller et al., 1993, Meth. Enzymol. 217: 581-599). These retroviral vectors have been to delete retroviral sequences that are not necessary for packaging of the viral genome and integration into host cell DNA. The nucleic acid sequences encoding antigenic peptides or antigenic fusion proteins to be used in gene therapy are cloned into one or more vectors, which facilitates delivery of the gene into a patient. More detail about retroviral vectors can be found in Boesen et al., 1994, Biotherapy 6: 291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Olin. Invest. 93: 644-651; Kiem et al., 1994, Blood 83: 1467-1473; Salmons and Gunzberg, 1993, human Gene Therapy 4: 129-141; and Grossman and Wilson, 1993, Cum Opin. in Genetics and Devel. 3: 110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3: 499-503 present a review of adenovirus-based gene therapy. Bout et al., 1994, human Gene Therapy 5: 3-10 demonstrated the use of adenovirus vectors to transfer genes to the respiratory epithelia of rhesus monkeys. Other instances of the use of adenoviruses in gene therapy can be found in Rosenfeld et al., 1991, Science 252: 431-434; Rosenfeld et al., 1992, Cell 68: 143-155; Mastrangeli et al., 1993, J. Clin. Invest. 91: 225-234; PCT Publication WO94/12649; and Wang, et al., 1995, Gene Therapy 2: 775-783. In a preferred embodiment, adenovirus vectors are used. Adeno-associated virus (AAV) has also been proposed for use in gene therapy (see, e.g, Walsh et al., 1993, Proc. Soc. Exp. Biol. Med, 204: 289-300; and U.S. Pat. No. 5,436,146).

Another approach to gene therapy involves transferring a nucleic acid molecule to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid molecule is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign nucleic acid molecules into cells (see, e.g., Loeffler and Behr, 1993, Meth. Enzymol. 217: 599-618; Cohen et al., 1993, Meth. Enzymol. 217: 618-644; Cline, 1985, Pharmac. Ther. 29: 69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, subject's state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the subject.

In an embodiment in which recombinant cells are used in gene therapy, nucleic acid sequences encoding the antigenic peptides or antigenic fusion proteins of the invention are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g., PCT Publication WO 94/08598, dated Apr. 28, 1994; Stemple and Anderson, 1992, Cell 71: 973-985; Rheinwald, 1980, Meth. Cell Bio. 21A: 229; and Pittelkow and Scott, 1986, Mayo Clinic Proc. 61: 771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

The invention also relates to methods for producing an antigenic peptide of the invention or an antigenic fusion protein of the invention comprising growing a culture of the cells of the invention in a suitable culture medium, and purifying the protein from the culture. For example, the methods of the invention include a process for producing an antigenic peptide or an antigenic fusion protein of the invention in which a host cell (i.e., a prokaryotic or eukaryotic cell) containing a suitable expression vector that includes a polynucleotide encoding an antigenic peptide or an antigenic fusion protein is cultured under conditions that allow expression of the encoded antigenic peptide or the encoded antigenic fusion protein. The antigenic peptide or the antigenic fusion protein can be recovered from the culture, conveniently from the culture medium, and further purified. The purified antigenic peptides or antigenic fusion proteins can be used in in vitro immunoassays which are well known in the art to identify anti-IgE antibodies which bind to the antigenic peptides or the antigenic fusion proteins.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBat® kit), and such methods are well known in the art, as described in Summers and Smith, Texas Agricultural Experiment Station Bulletin No. 1555 (1987), incorporated herein by reference. As used herein, an insect cell capable of expressing a polynucleotide of the present invention is "transformed."

Alternatively, an antigenic peptide of the invention or an antigenic fusion protein of the invention may also be expressed in a form which will facilitate purification. For example, an antigenic peptide may be expressed as fusion protein comprising a heterologous protein such as maltose binding protein (MBP) glutathione-S-transferase (GST) or thioredoxin (TRX) which facilitate purification. Kits for expression and purification of such fusion proteins are commercially available from New England BioLab (Beverly, Mass.), Pharmacia (Piscataway, N.J.) and in Vitrogen, respectively. The protein can also be tagged with an epitope and subsequently purified by using a specific antibody directed to such epitope. One such epitope ("Flag") is commercially available from Kodak (New haven, Conn.).

The antigenic peptides of the invention or the antigenic fusion proteins of the invention may also be expressed as a product of transgenic animals, e.g., as a component of the milk of transgenic cows, goats, pigs, or sheep which are characterized by somatic or germ cells containing a nucleotide sequence encoding the antigenic peptide or the antigenic fusion protein.

Any method known to those of skill in the art can be used to produce an antigenic peptide or an antigenic fusion protein of the invention At the simplest level, the amino acid sequence can be synthesized using commercially available peptide synthesizers. This is particularly useful in producing small peptides and fragments of larger polypeptides. The isolated antigenic peptides and antigenic fusion proteins of the invention are useful, for example, in generating antibodies against the native polypeptide.

One skilled in the art can readily follow known methods for isolating peptides and proteins in order to obtain one of the isolated antigenic peptides or antigenic fusion proteins of the present invention. These include, but are not limited to, immunochromatography, high performance liquid chromatography (hPLC), reverse-phase high performance liquid chromatography (RP-hPLC), size-exclusion chromatography, ion-exchange chromatography, and immuno-affinity chromatography. See, e.g., Scopes, Protein Purification: Principles and Practice, Springer-Verlag (1994); Sambrook et al., in Molecular Cloning: A Laboratory Manual; Ausubei et al., Current Protocols in Molecular Biology.

An antigenic peptide or an antigenic fusion protein of the invention is "isolated" or "purified" when it is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of a contaminating protein. When an antigenic peptide or an antigenic fusion protein of the invention is recombinantly produced, it is also preferably substantially free of culture medium, i.e., culture medium represents less than about 20%, 10%, or 5% of the volume of the protein preparation. When an antigenic peptide or an antigenic fusion protein of the invention is produced by chemical synthesis, it is preferably substantially free of chemical precursors or other chemicals, i.e., it is separated from chemical precursors or other chemicals which are involved in the synthesis of the antigenic peptide or the antigenic fusion protein. Accordingly such preparations of the protein have less than about 30%, 20%, 10%, 5% (by dry weight) of chemical precursors or compounds other than the antigenic peptide or the antigenic fusion protein.

The compositions of the invention are preferably tested in vitro, and then in vivo for the desired therapeutic or prophylactic activity, prior to use in humans. For example, in vitro assays which can be used to determine whether administration of a specific composition is indicated, include in vitro cell culture assays in which a patient tissue sample is grown in culture, and exposed to or otherwise administered a composition, and the effect of such composition upon the tissue sample is observed.

The expression of an antigenic peptide or an antigenic fusion protein can be assayed by the immunoassays, gel electrophoresis followed by visualization, or any other method known to those skilled in the art.

In various specific embodiments, in vitro assays can be carried out with representative cells of cell types involved in a patient's disorder, to determine if a composition has a desired effect upon such cell types. In accordance with the present invention, the functional activity of an antigenic peptide or an antigenic fusion protein can be measured by its ability to induce anti-IgE antibodies that inhibit IgE from binding to its receptor on mast cells or basophils in vitro without inducing the release of vasoactive substances such as histamine.

Compositions for use in therapy can be tested in suitable animal model systems prior to testing in humans, including but not limited to pigs, chicken, cows or monkeys.

The invention provides methods of treatment (and prophylaxis) by administration to a subject of an effective amount of a composition of the invention to elicit the production of anti-IgE antibodies which do not cause anaphylaxis. In a preferred aspect, a composition of the invention is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the composition comprises a nucleic acid are described above; additional appropriate formulations and routes of administration can be selected from among those described herein below.

Various delivery systems are known and can be used to administer a composition of the invention, e.g., encapsulation in Liposomes, microparticles, microcapsules, recombinant cells capable of expressing the composition, receptor-mediated endocytosis (see, e.g., Wu and Wu, 1987, J. Biol. Chem. 262: 4429-4432), construction of a nucleic acid as part of a retroviral or other vector, etc. Methods of introduction include but are not limited to intratumoral, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion, topical application, injection, or by means of an implant, said implant being of a porous, non-porous, or gelatinous material, including membranes, such as sialastic membranes, or fibers. In one embodiment, administration can be by direct injection at the site (or former site) of an allergic reaction.

In another embodiment, a composition of the invention can be delivered in a vesicle, in particular a liposome (see, e.g., Langer, 1990, Science 249: 1527-1533; Treat et al., in Liposomes in the Therapy of Infectious Disease and Cancer, Lopez-Berestein and Fidler (eds.), Liss, New York, pp. 353-365 (1989); and Lopez-Berestein, ibid., pp. 317-327; see generally ibid.)

In yet another embodiment, a composition of the invention can be delivered in a controlled release system. In one embodiment, a pump may be used (see, e.g., Langer, supra; Sefton, 1987, CRC Crit. Ref. Biomed. Eng. 14: 201; Buchwald et al., 1980, Surgery 88: 507; and Saudek et al., 1989, N. Engl. J. Med. 321: 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Pappas, 1983, J. Macromol. Sol, Rev. Macromol. Chem. 23: 61; see also Levy et al., 1985, Science 228: 190; During at al., 1989, Ann. Neurol. 25: 351; and howard et al., 1989, J. Neurosurg. 71: 105). In yet another embodiment, a controlled release system can be placed in proximity of the therapeutic target, thus requiring only a fraction of the systemic dose (see, e.g., Goodson, in Medical Applications of Controlled Release, supra, vol. 2, pp. 115-138 (1984)).

Other controlled release systems are discussed in the review by Langer (1990, *Science* 249: 1527-1533).

In a specific embodiment where the composition of the invention is a nucleic acid encoding an antigenic peptide or an antigenic fusion protein of the invention, the nucleic acid can be administered in vivo to promote expression of its encoded antigenic peptide or antigenic fusion protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliet et al., 1991, Proc. Natl. Acad. Sci. USA 88: 1864-1868), etc. Alternatively, a nucleic acid can be introduced intracellularly and incorporated within host cell DNA for expression, by homologous recombination.

The present invention also provides pharmaceutical compositions. Such compositions comprise a therapeutically effective amount of an antigenic peptide or an antigenic fusion protein of the invention, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or ph buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the antigenic peptide or the antigenic fusion protein, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The antigenic peptides or antigenic fusion proteins of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of cancer can be determined by known clinical techniques. In addition, in vitro assays may optionally be employed to help identify optimal dosage ranges. The precise dose to be employed in the formulation will further depend on the route of administration and the severity of the disease or disorder. however, suitable dosage ranges for intravenous administration are from about 20 to about 500 micrograms of active compound per kilogram body weight. Suitable dosage ranges for intranasal administration are from about 0.01 pg/kg body weight to about 1 mg/kg body weight. Effective doses can be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

EXAMPLES

1. Selection of Peptides and Conjugation to KLh

The CH3 domain of canine IgE as well as the junction between CH3 and CH4 domains formed the basis for selection of peptide vaccine candidates. Various nested and overlapping peptides were selected using computer programs for determination of appropriate antigenic properties including hydrophilicity, surface probability, flexibility, antigenic index, amphiphilic helix, amphiphilic sheet, and secondary structures. The peptides were synthesized and conjugated to KLh at Zymed Laboratories Inc. (San Francisco, Calif.) using cysteine-directed coupling method. The KLh-conjugated peptides were used to immunize rabbits at Zymed Laboratories Inc (South San Francisco). Peptides were also synthesized at W.M. Keck Biotechnology Resource Center (New haven, CT) with an N-terminal biotin residue without conjugation to KLh to provide material for use in ELISA to detect anti-peptide antibodies induced in animals immunized with the KLh-peptide conjugates. Preferred peptides of the present invention include peptides of Seq. ID#1 to Seq ID#14 and their homologous sequences from other IgE species.

2: Reactivity of Rabbit Anti-Peptide Antibodies with IgE-Derived Peptides

To test the ability of rabbit antisera to react with peptides of the present invention, an ELISA assay was developed as follows: Biotinylated IgE peptides were diluted to five μg/ml in coating buffer (Sodium Bicarbonate ph 9.0). Diluted peptides were added to the wells of a neutravidin plate (Pierce Chemical Co. Rockford, Ill.) at 100 μl/well and incubated at 4° C. overnight. Plates were washed 3× with phosphate-buffered saline containing 0.05% Tween-20 (PEST). Blocking buffer (2% skim milk in PBST) was added to each well at 200 μl/well and the plates were incubated at room temperature (RT) for 60 minutes, Plates were washed 3× with PBST. An 100 μl/well of 1:100 dilution of appropriate rabbit antisera were added to the top row of the appropriate wells and serum samples diluted 10 fold to the appropriate plate position. Plates were incubated at RT for 60 minutes. Plates were washed 3× with PEST. An 100 μl/well of a 1:20,000 dilution of a horse-radish peroxidase conjugated goat anti-rabbit IgG (KPL Laboratories, Gaithersburg, Md.) were added to each well and the plates incubated at RT for 60 minutes. Plates were washed 3× with PBST. A 100 μl/well of TMB microwell substrate (KPL; Gaithersburg, Md.) was added to each well and the plates incubated for 10-20 minutes at RT to allow for color development. The color development reaction was stopped with 50 μl/well of 0.18M sulfuric acid. The optical density (O.D.) of all wells was determined at wavelength of 450 nm using ELISA plate reader (Thermo Max; Molecular Devices, Sunnyvale, Calif.). As shown in FIG. 1, sera obtained from rabbits after immunization with the indicated peptides had a much higher reactivity to the respective peptides than that obtained by sera from rabbits prior to immunization with peptides of the present invention.

3. Reactivity of Rabbit Anti-Peptide Antibodies with Canine IgE

Canine IgE monoclonal antibodies (Bethyl laboratories; Montgomery; TX) was dispensed in the wells of 96-well plates at 1 ug/well in a volume of 100 μl. Plates were incubated at 4° C. overnight. Plates were washed 3× with PBST and 100 μl of blocking buffer (2% Skim milk in PBST) was added to each well and incubated at room temperature (RT) for 60 minutes. Plates were washed 3× with PBST and 1000/well of 1:200 dilution of appropriate rabbit antisera were added to the top row of the appropriate wells. Plates were incubated at RT for 60 minutes. Plates were washed 3× with PBST and 100 μl/well of a 1:10,000 dilution of a horseradish peroxidase conjugated goat anti-rabbit IgG (KPL Laboratories) was added to all wells. Plates were incubated at RT for 60 minutes. Plates were washed 3× with PBST and 100 μl/well of TMB substrate was added to each well. Color reaction was allowed to develop for 10-20 minutes. Color reaction was stopped by adding 50 μl/well of 0.18M sulfuric acid. Optical density of all wells was determined at 450 nm in an ELISA plate reader as above. As shown in FIG. 2, sera obtained from rabbits after immunization with the indicated peptides had a much higher reactivity to canine IgE than that obtained by sera from rabbits prior to immunization with peptides of the present invention.

4. In Vitro Degranulation Inhibition Assay

The development of an IgE vaccine rests on the identification of IgE peptides that induce antibodies which bind to soluble (free) IgE in serum and other bodily fluids, but do not cross-link receptor-bound IgE or release histamine from mast cells or basophils (i.e., non-anaphylactogenic antibodies). In order to assess the anaphylactogenic potential of antibodies raised against nested or overlapping sets of IgE-derived peptides such as those of the present invention, we developed an in vitro canine-specific degranulation assay based on rat basophilic cell line RBL-2h3 transfected with the high affinity receptor for canine IgE. When canine IgE is allowed to bind to its receptor on RBL2h3 cells and the receptor-bound IgE is incubated with anti-canine IgE antibodies, the receptor may be cross-linked (if anti-IgE antibodies bind to receptor-bound IgE) and this receptor cross-linking results in the release of histamine from rat cells. The amount of histamine released is a measure of the anaphylactic potential of anti-IgE antibodies. Conversely, the lack of histamine release indicates that the anti-dog IgE antibodies do not cross-link receptor bound-IgE and the peptide that induced the formation of these antibodies is suitable for use as a vaccine provided that the anti-peptide antibodies react with free IgE (e.g., IgE in serum or other fluids). Thus, the potential of any anti-IgE antibodies including antibodies raised against peptides of the present invention to effect release of histamine would be easily measured using this assay.

The gene encoding the high affinity receptor for dog IgE was assembled by the Polymerase Chain Reaction at ATG laboratories Inc (Eden Prairie, Minn.) and cloned into the pcDNA6 expression vector (In Vitrogen; CA). Rat RBL2h3 cell line (ATCC, Rockville Md.) was transfected with the pcDNA6 plasmid containing the gene encoding the canine IgE receptor using Fugene transfection reagent according to the manufacturer's recommendation (Beohringer Mannheim). RBL-2h3 cell lines expressing the dog high affinity receptor was selected and maintained in media containing 10 ug/ml blasticidin. The ability of canine IgE to bind to the transfected rat cells was confirmed by various assays including Flow cytometry and cell-based ELISA.

5. Ascaris Sensitization and Immunization

The effect of vaccination with peptides of the present invention on IgE-mediated reactions was evaluated in a study of IgE-mediated skin wheal reactivity induced in animals following sensitization to ascaris extract. The study design is outlined in table 1 and the study was conducted according to the following procedures:

1) Pre-sensitization procedures: Prior to commencement of the study (day −7), 5 ml of blood samples were collected from the jugular vein of each dog into serum separator tubes (SST). Serum was stored at −20 C. Skin tests were performed on all dogs by intradermal (ID) injection of Asc-1 allergen (Greer laboratories). ID injections were carried out on the shaved side/belly of each dog. Each animal received 6 injections representing 10-fold serial dilution of Asc-1 allergen (50 μg-0.5 ng), one injection of 0.1 μg histamine (positive control) and one injection of phosphate-buffered saline (PBS; negative control). Each injection is in a volume of 100 μl. Skin response was based on size of the area of wheal reaction. The wheal area was outlined, and the maximal dimension (major axis) and the dimension perpendicular to that (minor dimension) in millimeter are multiplied to calculate the wheal area. Skin responses were determined using metric rulers at 15 minutes following intradermal injection of allergen. To help visualize the wheal reaction, each dog was injected I/V with 5 ml of 1.0% solution of sterile Evan's blue dye approximately 5 minutes prior to skin tests.

2) Sensitization Schedule: Animals were injected with a mixture of 10 μg of Asc-1 and 2 mg of Rehydrogel (0.5 ml volume) and the mixture injected subcutaneously (SIC). At the same time animals were injected with 500 ng of Ricin (0.5 ml volume) intraperitoneally (I/P). The above injection regimens was repeated 5 more times; once every 2 weeks. Asc-1 and Ricin were dissolved in sterile PBS.

3) Post-sensitization skin test: Following the sensitization phase all dogs are evaluated for skin reactions. Skin tests were performed on all dogs as outlined under pre-sensitization skin test described above.

4) Vaccination: Animals in group F were not vaccinated. Animals in groups A, B, C, D, and E were vaccinated as described in table X. Animals are injected intramuscularly (I/M) with 1 ml of appropriate vaccine containing 50 μg of corresponding antigen.

5) Post-vaccination skin test: 14 days after the last vaccination, dogs were evaluated for skin reactions. Skin tests are performed on all dogs as outlined under pre-sensitization procedures.

6. Dog Anti-Peptide Antibodies

The induction of antibodies in dogs vaccinated with specific peptides of this invention is evaluated with an ELISA assay as follows: Peptides were diluted to 5 ug/ml in coating buffer (Sodium. Bicarbonate ph 9.0) and dispensed at 100 μl/well of neutravidin plates (Pierce). Plates were incubated at 4° C. overnight. Plates were washed 3× with PBST and 200 μl of blocking buffer (2% skim milk in PBST) was added to each well. Plates were incubated at RT for 60 minutes. Plates were washed 3× with PBST and 100 μl/well of 1:100 dilution of appropriate dog antisera was added to the top row of the appropriate wells. Serum samples were then diluted 10 fold to the appropriate plate position. Plates were incubated at RT for 60 minutes. Plates were washed 3× with PBST and 100 μl/well of a 1:20,000 dilution of a horse-radish peroxidase conjugated goat anti-dog IgG were added to each well. Plates were incubated at RT for 60 minutes. Plates were washed 3× with PBST and 100 μl/well of TMB substrate was added to all wells. Color reaction was allowed to develop for 10-20 minutes at RT. Color reaction was stopped by adding 50 μl/well of 0.18M sulfuric acid and optical density was read at 450 nm in ELISA Reader as above. As shown in table 2, sera obtained from dogs after immunization with the indicated peptides had a much higher reactivity to canine IgE than that obtained by sera from dogs prior to immunization with peptides of the present invention.

7. Skin Wheal Reactivity

The efficacy of peptides of the present invention in ameliorating IgE-mediated skin wheal reaction was determined by comparing the number of vaccinated animals in which there was a reduction or complete remission of the skin wheal reaction relative to the skin wheal reaction of the same animals prior to vaccination. The skin wheal reactivity of dogs following intradermal injection of ascaris extract is determined by injection of 100 μl of serial 10 fold dilutions (50 μg to 0.5 ng) of ascaris extracts as well as PBS and histamine (0.1 μg/site). The size of the wheal reaction is determined as the product of the major and minor axis of the wheal measured in millimeters using metric rulers. As can be seen from table 3, vaccination of animals with a cocktail of peptides derived from the CH3/CH4 domains (SeqID1-4) result in complete remission of skin wheal reaction in approximately 60% of animals.

TABLE 1

Experimental design

| Group | Sensitization | Vaccination | # of dogs |
|---|---|---|---|
| A | Asc-1 | RBS-1 (SEQ ID NO: 1) | 7 |
| B | Asc-1 | RBS-2 (SEQ ID NO: 2) | 7 |
| C | Asc-1 | RBS-3 (SEQ ID NO: 3) | 7 |
| D | Asc-1 | RBS-4 (SEQ ID NO: 4) | 7 |
| E | Asc-1 | RBS-COC (SEQ ID NOS. 1-4) | 7 |
| F | Asc-1 | None (PBS) | 7 |

TABLE 2

ELISA reactivity of dogs following immunization with IgE peptides

| Group | IgE peptide | Pre-vaccination titer | Post-vaccination titer |
|---|---|---|---|
| A | RBS-1 | <100 | 1000 |
| B | RBS-2 | <100 | 200 |
| C | RBS-3 | <100 | 1000 |
| D | RBS-4 | <100 | 1000 |
| E | RBS-COC | <100 for RBS-1, 2, 3 and 4 | 1:1000 for RBS-1, 2, 3, and 4 |
| F | PBS | <100 | <100 |

TABLE 3

Skin wheal reactivity of dogs immunized with IgE peptides:

| Group | Antigen | Remission of skin wheal reaction |
|---|---|---|
| A | RBS-1 (SEQ ID NO: 1) | 0/7 |
| B | RBS-2 (SEQ ID NO: 2) | 0/7 |
| C | RBS-3 (SEQ ID NO: 3) | 2/7 |
| D | RBS-4 (SEQ ID NO: 4) | 2/7 |
| E | RBS-COC (SEQ ID NOS.: 1-4) | 4/7 |
| F | None (PBS) | 0/7 |

8. Food Allergy Model

In order to develop a food allergy model to evaluate the effect of the anti-IgE vaccines of the present invention, fifty dogs were sensitized to ascaris antigens following injection of ascaris extract and ricin and then challenged orally with ascaris extract as follows:

1. Pre-sensitization procedures: Skin tests were performed on all dogs by intradermal (ID) injection of Asc-1 allergen (Greer laboratories). ID injections were carried out on the shaved side/belly of each dog. Each animal received 6 injections representing 10-fold serial dilution of Asc-1 allergen (50 μg-0.5 ng), one injection of 0.1 μg histamine (positive control) and one injection of phosphate-buffered saline (PBS; negative control). Each injection is in a volume of 100 μl. Skin response was based on size of the area of wheal reaction. The wheal area was outlined, and the maximal dimension (major axis) and the dimension perpendicular to that (minor dimension) in millimeter are multiplied to calculate the wheal area. Skin responses were determined using metric rulers at 15 minutes following intradermal injection of allergen. To help visualize the wheal reaction, each dog was injected I/V with 5 ml of 1.0% solution of sterile Evan's blue dye approximately 5 minutes prior to skin tests 2. Sensitization Schedule: Animals were injected with a mixture of 10 μg of Asc-1 and 2 mg of Rehydrogel (0.5 ml volume) and the mixture injected subcutaneously (SIC). At the same time, animals were injected with 500 ng of Ricin (0.5 ml volume) intraperitoneally (I/P), The above injection regimens was repeated 4 more times, once every 2 weeks. Asc-1 and Ricin were dissolved in sterile PBS.

3. Post-sensitization skin test: Following the sensitization phase all dogs were evaluated for skin reactions. Skin tests were performed on all dogs as outlined under pre-sensitization skin test described above.

4. Oral challenge: 14 days following the last skin test, dogs were given 2 mg of ascaris extract dissolved in 1 ml of distilled water via the oral route. Dogs were observed for signs of food allergy including vomiting and diarrhea. The results of oral challenge show that approximately 50% of sensitized dogs respond with clinical signs of allergy with every oral challenge.

9. Flea Allergy Model

To evaluate the capacity of ricin to accelerate the development of flea allergy dermatitis in dogs, a sensitization protocol in which dogs are sensitized to flea allergens in presence or absence of ricin is conducted as follows:

1. Five dogs are used as non-flea infested controls

2. Five dogs are exposed to fleas on a continual basis by infesting each dog with 16 fleas on day 0 and then 16-17 more fleas every other day for 12 weeks (last infestation day 84). Total flea exposure is 709 fleas.

3. Fifteen dogs are exposed to fleas episodically by infesting dogs with 109 fleas on day 0 and then 100 fleas every other week for 12 weeks (709 total fleas). Following a 48-hour infestation/exposure period fleas are removed. This allows for a 12-day nonexposure period between each reinfestation. Fleas are removed from dogs by the oral administration of nitenpyram (Capstar: Novartis Animal health; dogs<11.4 kg administered a 11.4 mg tablet, dogs>11.4 kg administered a 57 mg tablet.) Studies have determined that the product produces 100% mortality of fleas on dogs within 4 hours and is then rapidly eliminated from dogs with a T % (half-life) of 2.8 hours.

4. Fifteen dogs are exposed to fleas episodically by infesting dogs with 109 fleas on day 0 and then 100 fleas every other week for 12 weeks (709 total fleas). Following a 48-hour infestation/exposure period fleas are removed. This allows for a 2-day nonexposure period between each reinfestation. Fleas are removed from dogs by the oral administration of nitenpyram as described above. In addition to flea exposure all dogs receive an intraperitoneal injection of ricin (500 ng in 0.5 ml of sterile saline from a 1 mg/ml stock solution) on day 0. Dogs not showing a significant rise in serum IgE titers (on Day 14) from presensitization levels (prior to flea exposure) are given a second injection of ricin on day 28. Ricin injection may be repeated as necessary to induce anti-Fleas IgE in dogs.

All of references cited herein are which incorporated herein in their entirety by reference.

The present invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the claims.

The invention claimed is:

1. A pharmaceutical composition comprising an immunogenically effective amount of one or more isolated antigenic fusion proteins consisting of the amino acid sequence of SEQ ID NO: 11 and a heterologous carrier protein, wherein said fusion protein induces a non-anaphylactic anti-IgE immune response when administered to an animal.

2. The pharmaceutical composition of claim 1 further comprising one or more pharmaceutical carriers.

3. The pharmaceutical composition according to claim 1 or 2 further comprising an adjuvant.

4. The pharmaceutical composition according to claim 1 or 2 for the treatment of IgE-mediated allergic disorders.

5. The pharmaceutical composition of claim 3 for the treatment of IgE-mediated allergic disorders.

6. The pharmaceutical composition of claim 4, wherein the IgE-mediated allergic disorder is selected from the group consisting of asthma, allergic rhinitis, gastrointestinal allergies, food allergies, eosinophilia, conjunctivitis, glomerular nephritis and graft-versus-host disease.

7. The pharmaceutical composition of claim 5, wherein the IgE-mediated allergic disorder is selected from the group consisting of asthma, allergic rhinitis, gastrointestinal allergies, food allergies, eosinophilia, conjunctivitis, glomerular nephritis and graft-versus-host disease.

8. A polynucleotide sequence encoding the antigenic fusion protein of claim 1.

9. A host cell containing an expression vector that includes the polynucleotide sequence according to claim 8.

10. A method for producing an antigenic fusion protein according to claim 1 comprising growing a culture of the host cell of claim 9 in a suitable culture medium, and purifying antigenic fusion protein from the culture.

* * * * *